United States Patent
Ford et al.

(10) Patent No.: US 6,709,840 B1
(45) Date of Patent: Mar. 23, 2004

(54) ANERGY ASSOCIATED GENES

(75) Inventors: Gregory Ford, Sunnyvale, CA (US); Debra Bloom, Sun Prairie, WI (US); C. Garrison Fathman, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 09/854,300

(22) Filed: May 11, 2001

Related U.S. Application Data

(60) Provisional application No. 60/203,513, filed on May 11, 2000.

(51) Int. Cl.$^7$ .................. C07H 21/04; C12P 21/06; C12N 1/20; C12N 15/74
(52) U.S. Cl. .............. 435/69.1; 435/252.3; 435/320.1; 536/23.5; 536/24.31; 536/24.33
(58) Field of Search ..................... 536/23.5, 24.31, 536/24.33; 435/69.1, 252.03, 320.1

(56) References Cited

U.S. PATENT DOCUMENTS

| | | | |
|---|---|---|---|
| 5,445,934 A | | 8/1995 | Fodor et al. |
| 5,534,631 A | | 7/1996 | Li et al. |
| 5,747,299 A | * | 5/1998 | Bloom et al. |
| 5,989,549 A | * | 11/1999 | Sullivan et al. |

FOREIGN PATENT DOCUMENTS

| | | |
|---|---|---|
| WO | WO95/35505 | 12/1995 |
| WO | WO 20005367 A2 * | 2/2000 |

OTHER PUBLICATIONS

Attwood et al., The babel of bioinformatics, Oct. 2000, Science 290 (5491): 471–473.*
Mikayama et al, Molecular cloning and functional expression of a cDNA encoding gycosylation-inhibting factor, Nov. 1993, Proc. Natl. Acad. Sci, USA Vol 90: 10056–10060.*
Sambrook et al in Molecular Cloning, 1989, Cold Spring Harbor Laboratory, CSH, NY, Ch. 11 &17.*
Wallace et al in Methods Enzymol 152: 432–439, 1987.*
Voet et al., Biochemistry I, 1990, pp. 126–234.*
Database GenBank (EST); Accession No: A1987883; Marra et al. mouse clone; Sep. 2, 1999; Having at least 18 and 50 contiguous nucleotides of SEQ ID NO: 5.
Database SPTREMBL; Accession No: 076671; Nov. 1, 1998; Wilson et al. H10E21.5 Protein; Having a Fragment of at Least 12 Amino Acids of SEQ ID NO:6.

Roep, Bart O. (Sep. 1996), "T–Cell Responses to Autoantigens in IDDM—The Search for the Holy Grail." *Diabetes*, vol. 45:1147–1156.
Boussiotis et al. (Feb. 2000), "p27$^{kip1}$ Functions as an Energy Factor Inhibiting Interleukin 2 Transcription and Clonal Expansion of Alloreactive Human and Mouse Helper T Lymphocytes." *Nature Medicine*, vol. 6(2):290–297.
Drmanac et al. (Jun. 11, 1993), "DNA Sequence Determination by Hybridization: A Strategy for Efficient Large–Scale Sequencing." *Science*, vol. 260:1649–1652.
Fields et al. (Mar. 1, 1996), "Blocked Ras Activation in Anergic CD4$^+$ T Cells." *Science*, vol. 271:1276–1278.
Harding et al. (Apr. 16, 1992), "CD28–Mediated Signalling Co–Stimulates Murine T Cells and Prevents Induction of Anergy in T Cell Clones." *Nature*, vol. 356:607–609.
Kang et al. (Aug. 21, 1992), "Transactivation by AP–1 is a Molecular Target of T Cell Clonal Anergy." *Science*, vol. 257:1134–1138.
Korthäuer et al. (2000), "Anergic T Lymphocytes Selectively Express an Integrin Regulatory Protein of the Cytohesin Family." *Journal of Immunology*, vol. 164:308–318.
Hautamaa et al. (Jun. 1997), "Murine Lymphotactin: Gene Structure, Post–Translational of Expression by CD28 Costimulation." *Cytokine*, vol. 9(6):375–382.
Powell et al. (1998), "Molecular Regulation of Interleukin–2 Expression by CD28 Co–Stimulation and Anergy." *Immunological Reviews*, vol. 165:287–300.

* cited by examiner

*Primary Examiner*—Christina Chan
*Assistant Examiner*—Phuong Huynh
(74) *Attorney, Agent, or Firm*—Pamela J. Sherwood; Bozicevic, Field & Francis LLP

(57) ABSTRACT

Isolated nucleic acid compositions and sequences of anergy associated genes are provided, including the novel GRAIL gene. Expression of these genes is upregulated during the early stages of induction of anergy. The murine GRAIL sequence is shown to attenuate IL-2 transcription in T cells during response to antigenic stimulation. The identification of genes involved in the induction of anergy is useful in the evaluation of the pathophysiology or immunotherapy of cancer, autoimmune disease, and transplant rejection. Genetic sequences involved in anergy induction are useful markers in the evaluation of specific immunotherapies. Functional characterization of genes involved in anergy induction allows the elucidation of the mechanism(s) of T cell anergy, including the transcriptional blockade of IL-2, which may be manipulated to regulate T cell responses in human disease. The signaling pathways involving GRAIL are of significant interest in the identification of drugs that either block or upregulate the function(s) of GRAIL.

6 Claims, 10 Drawing Sheets

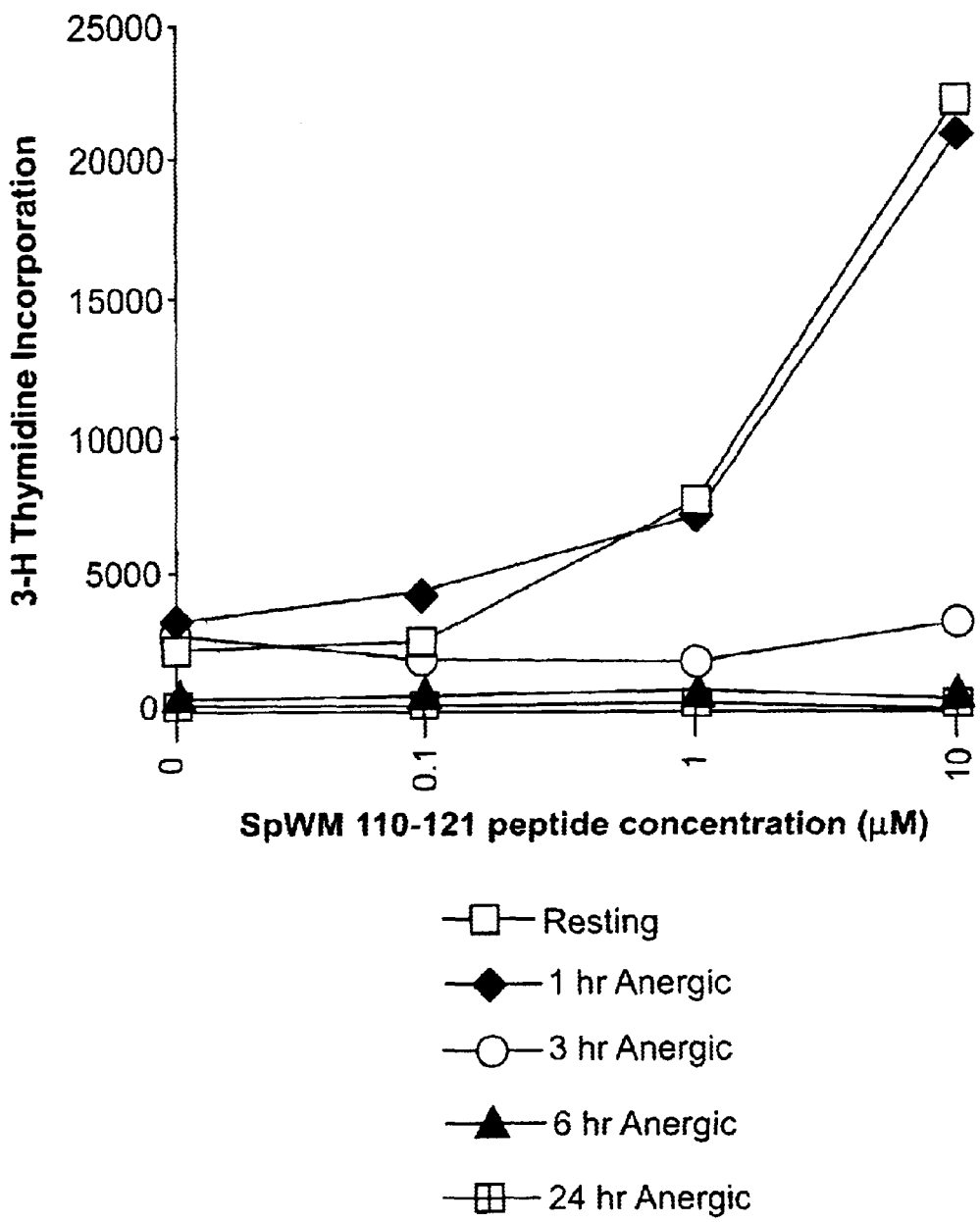

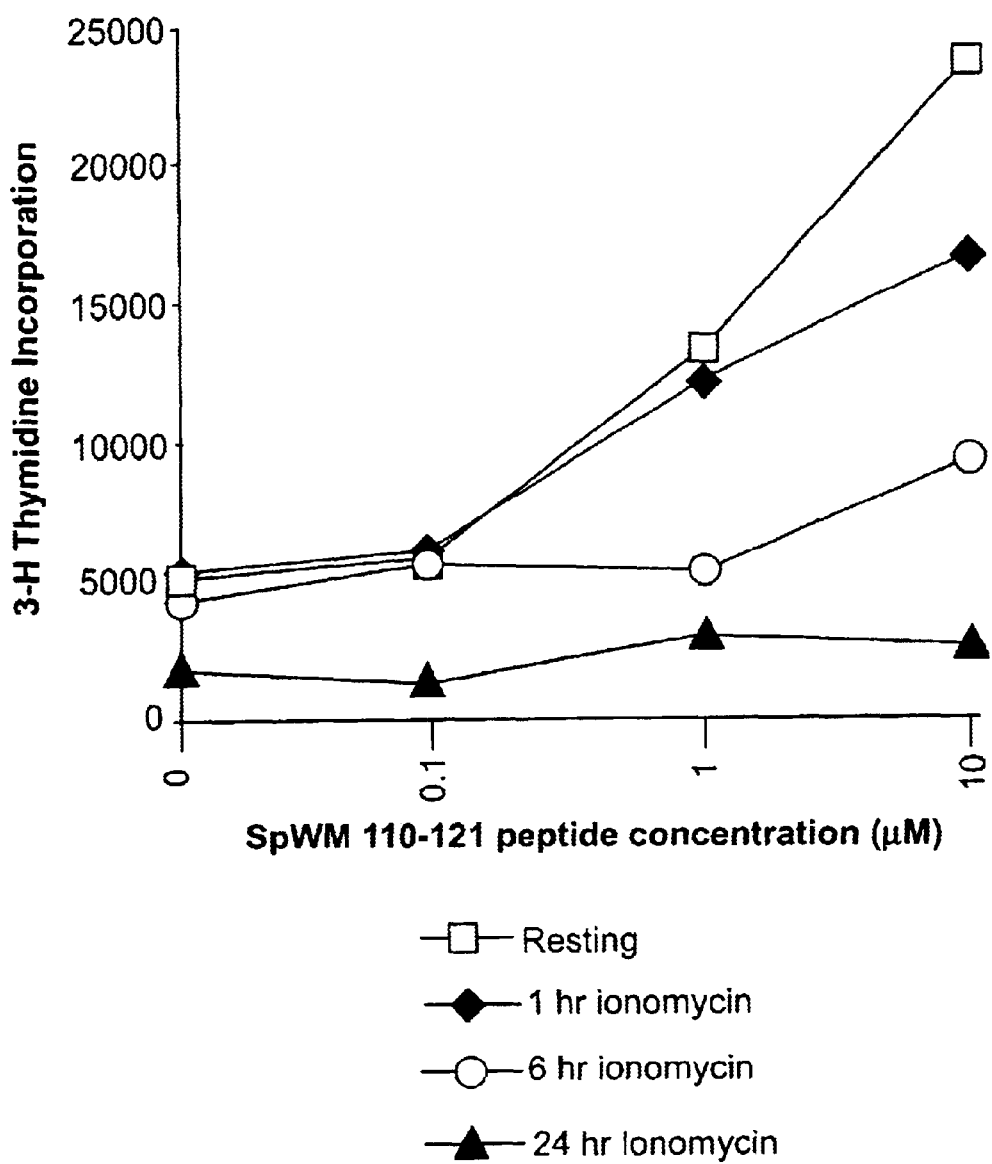

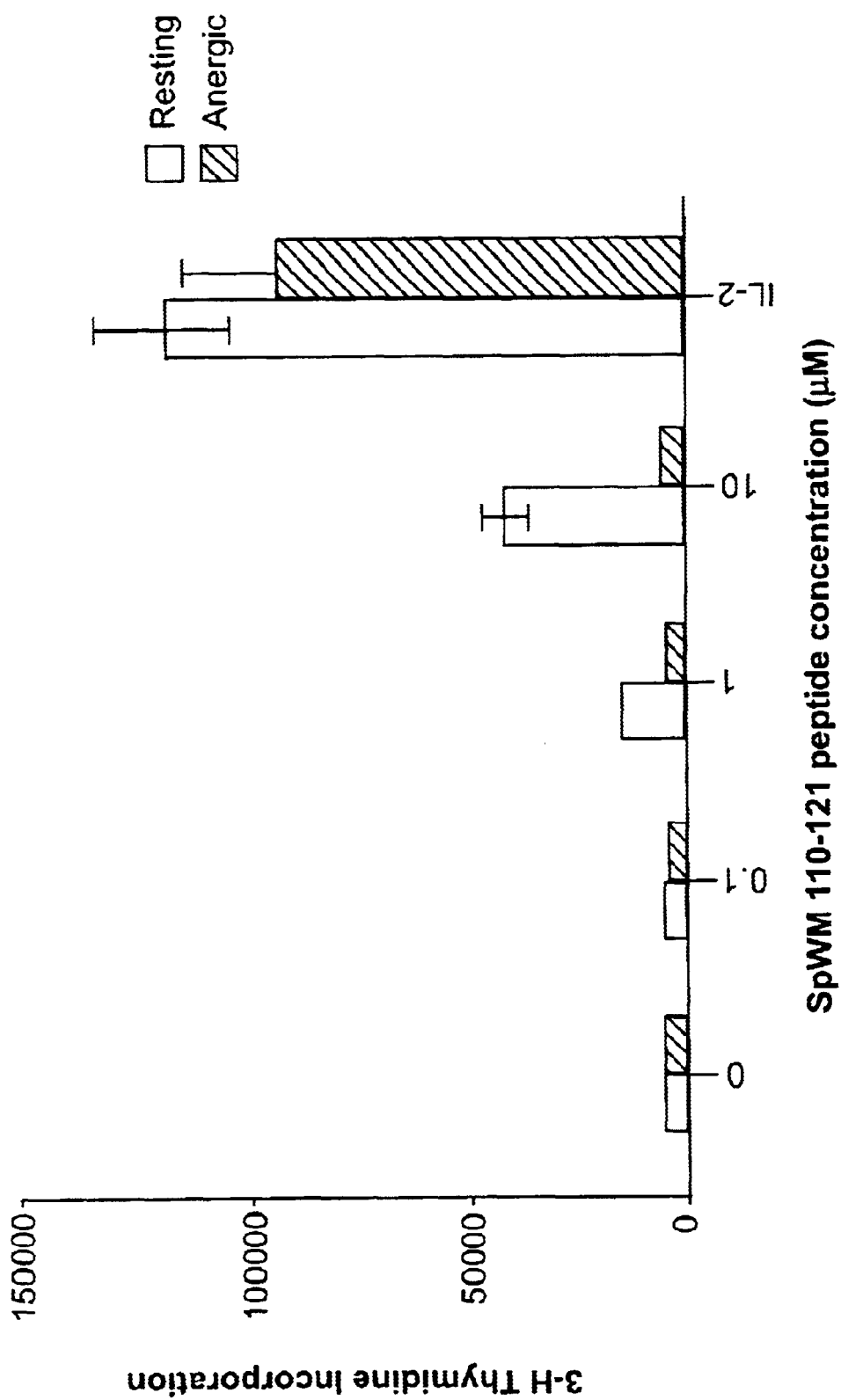

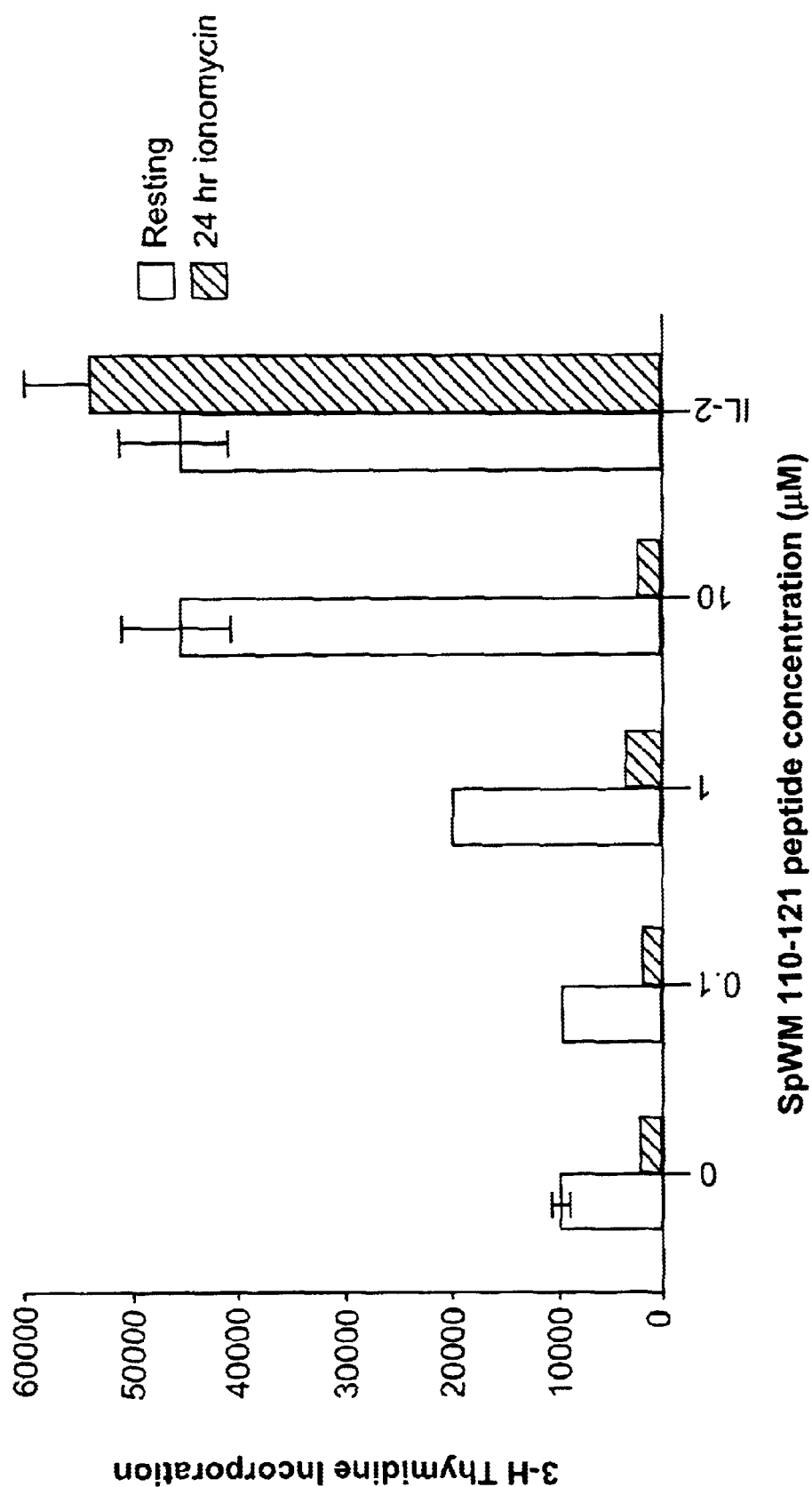

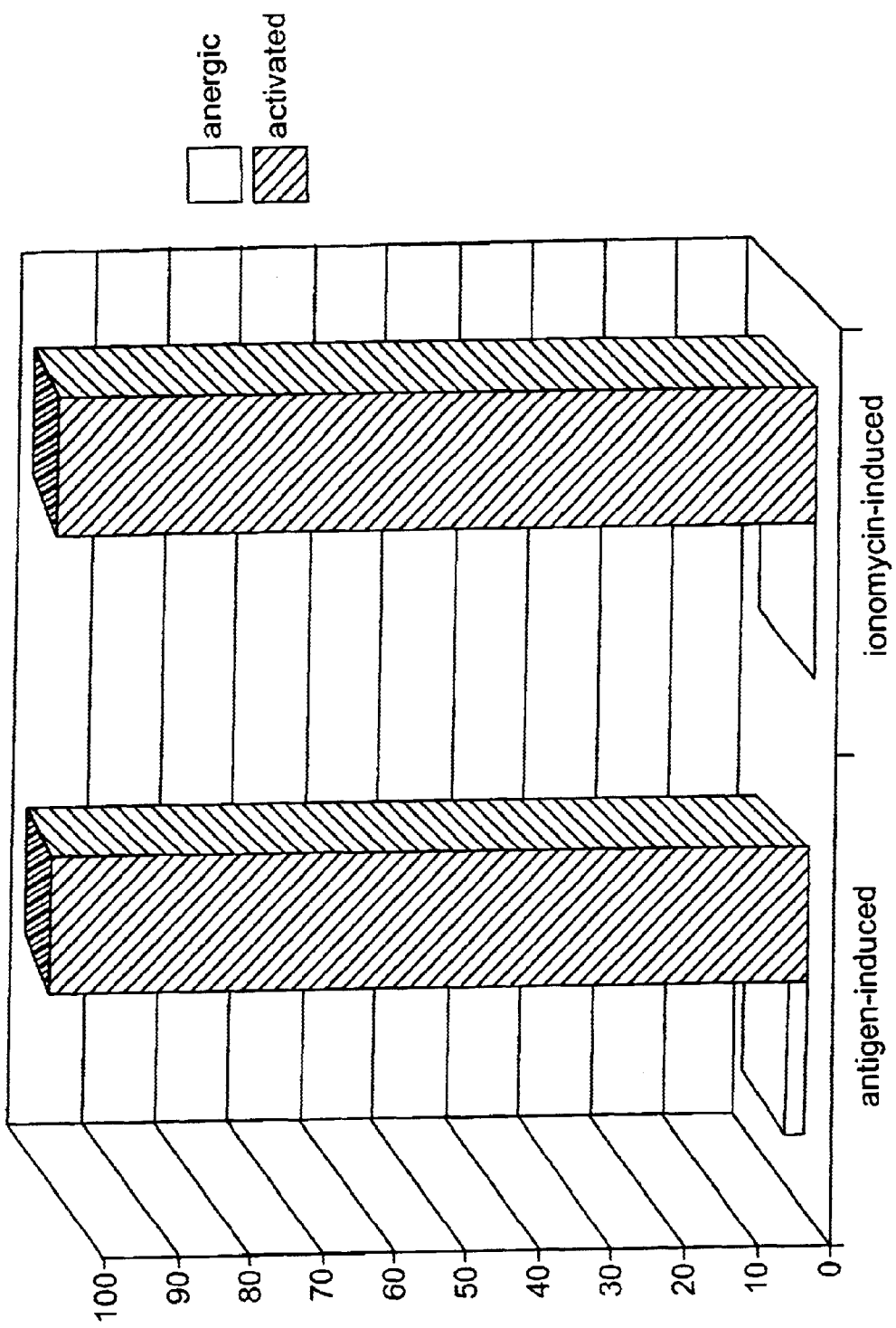

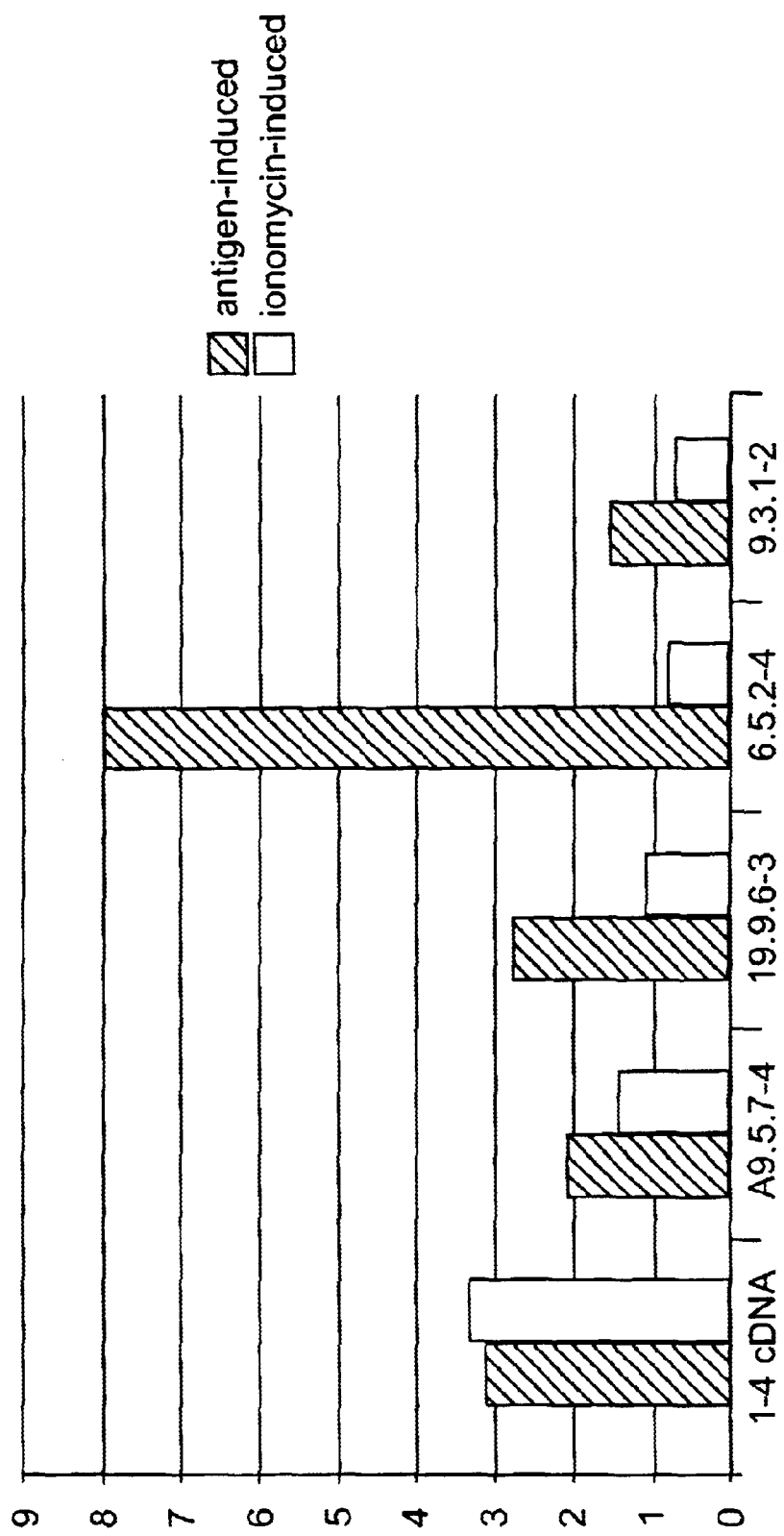

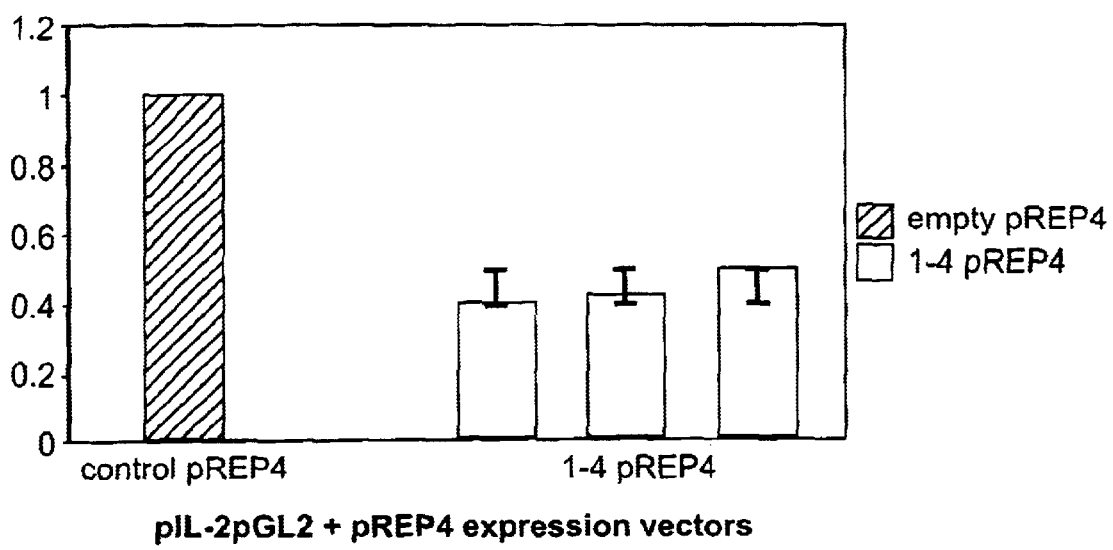

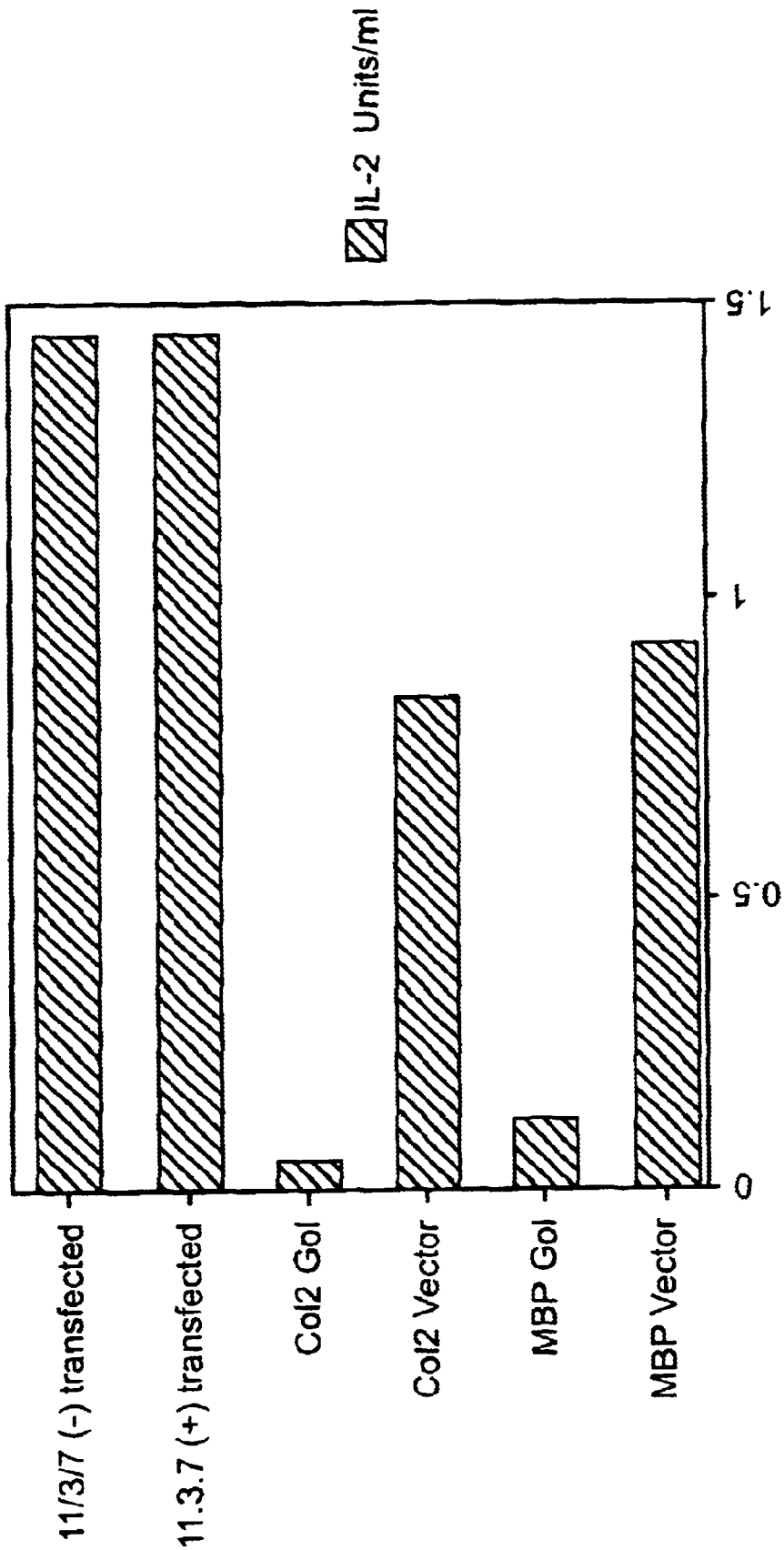

ANERGY ASSOCIATED GENES

CROSS-REFERENCE TO RELATED APPLICATIONS

The present application claims the benefit of priority to U.S. Provisional Patent Application No. 60/203,513, filed May 11, 2000.

GOVERNMENT SUPPORT

This work is supported at least in part by grants from the N.I.H. grant CA 65237-10; and an Immunology Training Fellowship (PHS Award AI07290-14). The government may have certain rights in this invention.

INTRODUCTION

The dynamics of the immune system have an enormous impact on an individual's health and well-being. T cells, the regulators of immune response, have a particularly important role, in determining when, or if, to mount a response against a particular antigen. Inappropriate T cell response to self-antigens can be deadly, and so several mechanisms serve to establish tolerance. These are broadly grouped into central; or peripheral tolerance.

Unlike central tolerance, in which auto-reactive T cell are deleted; peripheral tolerance involves induction of an unresponsive state, termed anergy. The anergic state is induced through a partial activation process (Harding et al. (1992) *Nature* 370:607–609). When peripheral T cells encounter antigen, they are normally presented with two molecular signals. The first signal is binding of the T cell antigen receptor to a peptide antigen presented by an MHC class II molecule. The second, or "costimulatory" signal, is provided by interaction of B7 like molecules on the antigen presenting cell (APC) with the CD28 receptor on the T cell. Antigen stimulation in the absence of sufficient costimulatory signals results in anergy. Anergic T cells are characterized by greatly reduced or absent IL-2 production, and a lack of proliferation in response to full activation.

There is a therapeutic interest in understanding the mechanisms that underlie anergy. Loss of anergy in T cells that recognize self-antigens can lead to autoimmune diseases such as insulin dependent diabetes, rheumatoid arthritis, and multiple sclerosis. In one example of a therapeutic use, the anergy inducing molecule CTLA4Ig has been tested in clinical trials for the treatment of the autoimmune disease psoriasis vulgaris. Conversely, inappropriate anergy may be associated with cancer, where the body fails to mount a response to tumor antigens.

Although it has been well established that TCR signaling in the absence of CD28 costimulation leads to T cell anergy, the actual mechanism(s) of anergy induction are not well characterized. It has been shown, for example, that anergized T cells exhibit a blockade in intracellular signaling pathways leading to IL-2 gene transcription, which may be attributed to diminished nuclear translocation of the transcription factor AP-1, Kang et al. (1992) *Science* 257:1134–1138). It has also been demonstrated that the Ras signaling pathway, which ultimately leads to AP-1 translocation, may be "defective" in anergized T cells (Fields et al. (1996) *Science* 271:1276–1278). While these studies suggested that blockade of certain signaling pathways was involved in the functional state of anergy, they did not address whether early changes in gene expression were involved in anergy induction. The further identification and evaluation of genes involved in the induction and maintenance is therefore of great clinical and scientific interest.

Relevant Literature

One tool showing considerable promise for expression analysis is the nucleic acid array, reviewed by Ramsay (1998) *Nat. Biotech.* 16:40–44. These arrays contain dense collections of nucleic acids, either PCR products or oligonucleotides, usually of known sequence, that have been either synthesized or printed at fixed spatial locations on suitable substrates, such as nylon filters or glass slides. When labeled DNA or RNA samples are hybridized to the arrays, the abundance of specific sequences in solution can be quantitated based on the fluorescent or radioactive signal intensity at the position of the complementary probe. A number of methods are available for creating microarrays of biological samples, exemplary are PCT Application Ser. No. WO95/35505, published Dec. 28, 1995; U.S. Pat. No. 5,445,934, issued Aug. 29, 1995; and Drmanac et al., *Science* 260:1649–1652.

Changes in gene expression related to anergy have been explored in the literature. Bousslotis et al. (2000) *Nat Med* 6(3):290–7 report that p27kip1 cyclin-dependent kinase inhibitor is involved in the blockade of clonal expansion of anergic T cells. Korthauer et al. (2000) *J Immunol* 164(1):308–18 used differential display of reverse transcribed RNA to identify genes selectively induced in anergic T cells. Powell et al. (1998) *Immunol Rev* 165:287–300 report that T-cell anergy appears to be an active negative state in which IL-2 production is inhibited both at the level of signal transduction and by cis-dominant repression at the level of the IL-2 promoter.

Hautamaa et al. (1997) *Cytokine* 9(6):375–82 used a differential screening approach to clone murine lymphotactin from a cDNA library produced from an unresponsive Th1 cell.

SUMMARY OF THE INVENTION

Isolated nucleic acid compositions and sequences of anergy associated genes are provided, including the novel GRAIL gene. Expression of these genes is upregulated during the early stages of induction of anergy. The nucleic acid compositions find use in identifying homologous or related genes; in producing compositions that modulate induction or maintenance of anergy; for gene therapy; mapping functional regions of the encoded protein; and in studying associated physiological pathways. In addition, modulation of the gene activity in vivo is used for prophylactic and therapeutic purposes, such as treatment of autoimmune disease, identification of anergic T cells, and the like. The GRAIL sequence is shown to attenuate IL-2 transcription in T cells during; response to antigenic stimulation.

The identification of genes involved in the induction of anergy is useful in the evaluation of the pathophysiology or immunotherapy of cancer, autoimmune disease, and transplant rejection. Genetic sequences involved in anergy induction are useful markers in the evaluation of specific immunotherapies. Functional characterization of genes involved in anergy induction allows the elucidation of the mechanism(s) of T cell anergy, including the transcriptional blockade of IL-2, which may be manipulated to regulate T cell responses in human disease.

BRIEF DESCRIPTION OF THE DRAWINGS

FIG. 1. Kinetic analysis of anergy induction. (A) To examine the kinetics of TCR-induced anergy, 11.3.7 T cells were co-cultured with B7- RT 7.7 fibroblast cells at a 1:1 ratio with (anergic) or without (resting control) different concentrations of peptide for different lengths of time before positive selection of T cells by magnetic separation with anti-CD4 microbeads. A standard proliferation assay was then used to test the antigenic responsiveness of selected resting or anergic cells. (B) Murine rIL-2 was added to cultures at 5 Units/ml (during the period of restimulation) to test for anergized T cell viability. (C) To examine the kinetics of ionomycin-induced anergy induction, 11.3.7 T cells were co-cultured with or without 1.5 μM ionomycin for 1, 6 or 24 hours and analyzed by proliferation assays. (D) As before, murine rIL-2 was added to cultures at 5 Units/ml (during the period of restimulation) to test for viability.

FIG. 2. Relative levels of IL-2 mRNA in anergic or activated 11.3.7 T cells. The relative quantity of IL-2 message in anergic and activated RNA samples was determined by quantitative PCR using IL-2 specific primers and an IL-2-specific fluorogenic probe. Message levels in anergic and activated cells were compared by setting the IL-2 expression in activated cells to 100% and calculating the anergic T cell expression as a percentage of that level.

FIG. 4 shows a comparison of mRNA expression levels between the antigen-induced and ionomycin-induced models of anergy. The ratio of anergic:activated (fold-induction) mRNA levels for the different ddPCR clones is compared between the two models of anergy induction.

FIGS. 5A and 5B show the attenuation of IL-2 transcription in response to T cell activation by the GRAIL gene.

DETAILED DESCRIPTION OF THE EMBODIMENTS

Figure 3A:
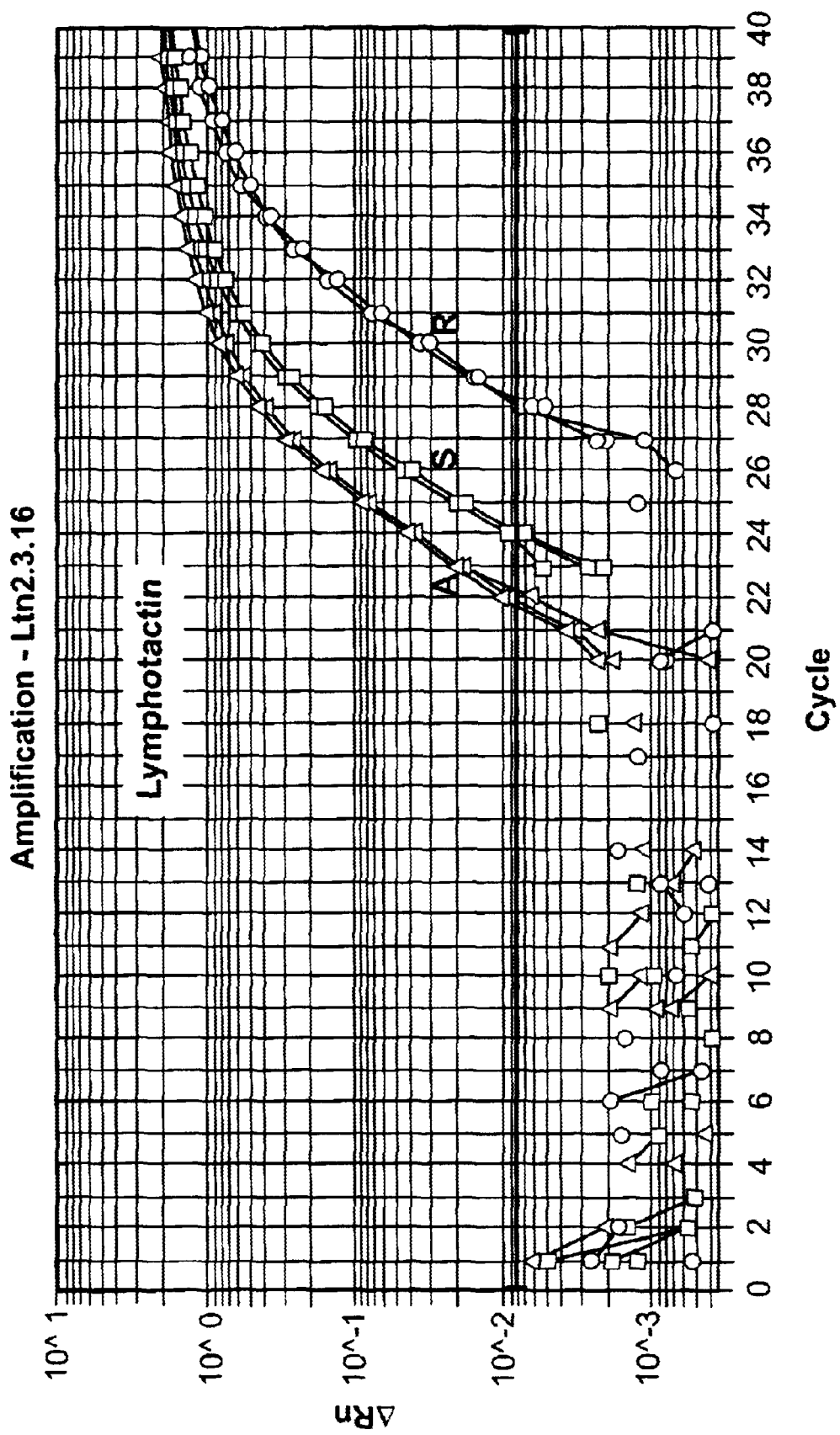
FIG. 3. Representative "real-time" PCR experiment showing the differential expression of clone 6.5.2-4 (lymphotactin). (A) Equivalent amounts of cDNA from anergic (A), activated (S), or resting (R) 11.3.7 T cells was amplified using primers and a fluorogenic probe specific for the 6.5.2-4 ddPCR product. The change in reporter dye fluorescence (measured by the ABI PRISM 7700 Sequence Detection System) ($\Delta R_n$, y-axis) is plotted against the PCR cycle number (x-axis). The observed shift to the left of the anergic (A) curve indicates a reduction in the number of PCR cycles required to reach a certain threshold fluorescence level ($C_T$) which also indicates an increased level of input 6.5.2-4 RNA in anergic T cells. (B) The same cDNAs were amplified in separate PCR reactions with primers and a probe specific for the GAPDH message. Virtually identical curves for anergic (A), activated (S), and resting (R) samples indicate equivalent levels of total input RNA into PCR samples.

Methods and compositions are provided for the expression analysis of anergic cells and the induction or maintenance of anergy. Included are nucleic acid sequences of the novel anergy associated gene, GRAIL. Expression of GRAIL and other anergy associated genes is upregulated during the early stages of induction of anergy in T cells. Modulation of expression of such genes, particularly of the GRAIL gene, is useful in manipulating the anergic state. When constitutively expressed in T cells, GRAIL attenuates the increased transcription of IL-2 normally found in response to stimulation.

The provided genetic sequences find use, alone or in combinations, (e.g. as arrays of polynucleotides), in determining the expression profile of cells relating to anergy. For example, in the screening of candidate biologically active compounds for modulation of T cell anergy, the sequences may be used to determine the effect of the agent on anergy related gene expression.

Target identification for drug discovery or screening utilizes GRAIL expression, or the pathway(s) downstream of GRAIL activation, for novel drug identification and development. For example, expression of GRAIL has been found to block tyrosine phosphorylation of a protein present in T cells during activation.

Sequences of the invention include the following:

| reference | SEQ ID NO | |
|---|---|---|
| 9.3.1-2 | 1 | MRC-OX44 |
| 19.9.6-3 | 2 | Nurr2 |
| 6.5.2-4 | 3 | lymphotactin |
| A9.5.7-4 | 4 | cbl-b |
| 1-4 | 5, 6 | murine GRAIL |
| | 7, 8 | human GRAIL |

Two assay systems were developed to determine the kinetics of anergy induction in vitro, which allowed analysis of changes in gene expression correlated with induction of anergy. The anergic phenotype was observed after as little as three hours of signaling through the TCR in the absence of co stimulation; as well as under conditions of ionomycin treatment. Using differential display of mRNA expression, five genes were identified whose increased expression was correlated with the induction of T cell anergy in vitro. Expression of two of these genes was also increased in T cells following ionomycin-induced anergy.

Characterization of Grail Gene

The GRAIL gene encodes a protein of approximately 50 kD, and migrates as a 2.75 K mRNA on northern blots. The nucleotide and amino acid sequence of the mouse homolog is provided as SEQ ID NO:5 and 6 and a sequence of the human GRAIL homolog is attached as SEQ ID NO:7 and SEQ ID NO:8, respectively, in the attached seqlist. The encoded murine GRAIL protein has a zinc RING finger domain (roughly located in the amino acid sequence SEQ ID NO:6 and 8, positions 339 to 413, with high degree of sequence similarity in position 360–410), which domain is believed to be in the cytoplasmic, C-terminal portion of the protein, and thus has some sequence similarity to other proteins having a zinc RING finger. RING domains have been found to mediate protein/protein interactions. The translated GRAIL protein also has sequences in the amino terminus that are indicative of a transmembrane domain(s).

GRAIL is expressed in multiple tissues, including T cells, heart, liver and kidney. In resting T cells, or activated T cells, expression is low, but is upregulated shortly after partial activation (anergic stimulation), i.e. binding of the T cell antigen receptor in the absence of a costimulatory signal. Expression remains high for a period of time after induction of anergy (>72 hours) and is found upregulated in islet infiltrating T cells of NOD mice in the pre-diabetic (presumably anergic) state. Expression of GRAIL (by transient transfection or retroviral transduction of CD4+T cells) reduces IL-2 mRNA and protein expression in response to stimulation of the T cells.

The human homolog of GRAIL was identified by using a fragment of the murine cDNA as a hybridization probe against a cDNA library from human liver, utilizing low stringency conditions. Additional homologs of GRAIL may be identified by similar screening strategies. For example, cDNA libraries from tissues that express GRAIL, such as liver, may be used for screening. The probe may be a large fragment, or one or more short degenerate primers. Such sequences are selected from regions that are not likely to diverge over evolutionary time and are of low degeneracy. The complementary binding sequence will usually be at least 14 nucleotides, preferably at least about 17 nucleotides and usually not more than about 30 nucleotides. Conveniently, amplification reactions are used to generate an initial probe, which can then be used to hybridize to a library; for rapid amplification of cloned ends (RACE); etc. One or more of the resulting clones may then be used to rescreen the library to obtain an extended sequence, up to and including the entire coding region, as well as the non-coding 5'- and 3'-sequences. As appropriate, one may sequence all or a portion of the resulting cDNA coding sequence.

Nucleic acids having sequence similarity to the provided GRAIL genetic sequences are detected by hybridization under low stringency conditions, for example, at 50° C. and 6×SSC (0.9 M NaCl/0.09 M Na citrate) and remain bound when subjected to washing at 55° C. in 1×SSC (0.15 M NaCl/0.015 M Na citrate). Sequence identity may be determined by hybridization under stringent conditions, for example, at 50° C. or higher and 0.1×SSC (15 mM NaCl/01.5 mM Na citrate). Nucleic acids having a region of substantial identity to the provided GRAIL sequences, e.g. allelic variants, genetically altered versions of the gene, etc., bind to the provided GRAIL sequences under stringent hybridization conditions. By using probes, particularly labeled probes of DNA sequences, one can isolate homologous or related genes. The source of homologous genes may be any species, e.g. primate species, particularly human; rodents, such as rats and mice, canines, felines, bovines, ovines, equines, yeast, nematodes, etc.

Between species in a group, e.g. human and mouse, homologs have substantial sequence similarity, i.e. at least 75% sequence identity between nucleotide sequences, in some cases 80 or 90% sequence identity, and may be as high as 95% sequence identity between closely related species. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990), J. Mol. Biol. 215:403–10. In general, variants of the invention have a sequence identity greater than at least about 65%, preferably at least about 75%, more preferably at least about 85%, and may be greater than at least about 90% or more as determined by the Smith-Waterman homology search algorithm as implemented in MPSRCH program (Oxford Molecular). Exemplary search parameters for use with the MPSRCH program in order to identify sequences of a desired sequence identity are as follows: gap open penalty: 12; and gap extension penalty: 1.

Grail Nucleic Acid Compositions

Nucleic acids encoding GRAIL may be cDNA or genomic DNA or a fragment thereof. The term "GRAIL gene" shall be intended to mean the open reading frame encoding specific GRAIL polypeptides, introns, as well as adjacent 5' or 3' non-coding nucleotide sequences involved in the regulation of expression, up to about 20 kb beyond the coding region, but possibly further in either direction. The gene may be introduced into an appropriate vector for extrachromosomal maintenance or for integration into the host.

The term "cDNA" as used herein is intended to include all nucleic acids that share the arrangement of sequence elements found in native mature mRNA species, where sequence elements are exons and 3' and 5' non-coding regions. Normally mRNA species have contiguous exons, with the intervening introns, when present, removed by nuclear RNA splicing, to create a continuous open reading frame encoding a GRAIL protein.

A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The sequence of the 5' flanking region may be utilized for promoter elements, including enhancer binding sites, that provide for developmental regulation in tissues where GRAIL is expressed. The tissue specific expression is useful for determining the pattern of expression, and for providing promoters that mimic the native pattern of expression. Naturally occurring polymorphisms in the promoter region are useful for determining natural variations in expression, particularly those that may be associated with disease.

Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995) *Mol Med* 1: 194–205; Mortlock et al. (1996) *Genome Res.* 6: 327–33; and Joulin and Richard-Foy (1995) *Eur J Biochem* 232: 620–626.

The regulatory sequences may be used to identify cis acting sequences required for transcriptional or translational regulation of GRAIL expression, especially in different tissues or stages of development, and to identify cis acting sequences and trans acting factors that regulate or mediate GRAIL expression. Such transcription or translational control regions may be operably linked to a GRAIL gene in order to promote expression of wild type or altered GRAIL or other proteins of interest in cultured cells, or in embryonic, fetal or adult tissues, and for gene therapy.

The nucleic acid compositions of the subject invention may encode all or a part of the subject polypeptides. Double or single stranded fragments may be obtained of the DNA sequence by chemically synthesizing oligonucleotides in accordance with conventional methods, by restriction enzyme digestion, by PCR amplification, etc. For the most part, DNA fragments will be of at least 15 nt, usually at least 18 nt, more usually at least about 50 nt. Such small DNA fragments are useful as primers for PCR, hybridization screening probes, etc. Larger DNA fragments, i.e. greater than 100 or 250 nt are useful for production of the encoded polypeptide. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The GRAIL genes are isolated and obtained in substantial purity. generally as other than an intact, naturally occurring chromosome. Usually, the DNA will be obtained substantially free of other nucleic acid sequences that do not include a GRAIL sequence or fragment thereof, generally being at least about 50%, usually at least about 90% pure and are typically "recombinant", i.e. flanked by one or more nucleotides with which it is not normally associated on a naturally occurring chromosome.

The DNA may also be used to identify expression of the gene in a biological specimen. The manner in which one probes cells for the presence of particular nucleotide sequences, as genomic DNA or RNA, is well established in the literature and does not require elaboration here. DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of GRAIL gene expression in the sample.

The sequence of a GRAIL gene, including flanking promoter regions and coding regions, may be mutated in various ways known in the art to generate targeted changes in promoter strength, sequence of the encoded protein, etc. The DNA sequence or protein product of such a mutation will usually be substantially similar to the sequences provided herein, i.e. will differ by at least one nucleotide or amino acid, respectively, and may differ by at least two but not more than about ten nucleotides or amino acids. The sequence changes may be substitutions, insertions or deletions. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used.

Techniques for in vitro mutagenesis of cloned genes are known. Examples of protocols for site specific mutagenesis may be found in Gustin et al., *Biotechniques* 14:22 (1993); Barany, *Gene* 37:111–23 (1985); Colicelli et al., *Mol Gen Genet* 199:537–9 (1985); and Prentki et al., *Gene* 29:303–13 (1984). Methods for site specific mutagenesis can be found in Sambrook et al., *Molecular Cloning: A Laboratory Manual,* CSH Press 1989, pp. 15.3–15.108; Weiner et al., *Gene* 126:35–41 (1993); Sayers et al., *Biotechniques* 13:592–6 (1992); Jones and Winistorfer, *Biotechniques* 12:528–30(1992); Barton et al., *Nucleic Acids Res* 8:7349–55(1990); Marotti and Tomich, *Gene Anal Tech* 6:67–70 (1989); and Zhu, *Anal Biochem* 177:120–4 (1989). Such mutated genes may be used to study structure-function relationships of GRAIL, or to alter properties of the protein that affect its function or regulation.

Grail Polypeptides

The subject gene may be employed for producing all or portions of GRAIL polypeptides. For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to a GRAIL gene, or may be derived from exogenous sources.

The peptide may be expressed in prokaryotes or eukaryotes in accordance with conventional ways, depending upon the purpose for expression. For large scale production of the protein, a unicellular organism, such as *E. coli, B. subtilis, S. cerevisiae,* insect cells in combination with baculovirus vectors, or cells of a higher organism such as vertebrates, particularly mammals, e.g. COS 7 cells, may be used as the expression host cells. In some situations, it is desirable to express the GRAIL gene in eukaryotic cells, where the GRAIL protein will benefit from native folding and post-translational modifications. Small peptides can also be synthesized in the laboratory. Peptides that are subsets of the complete GRAIL sequence, e.g. peptides of at least about 8 amino acids in length, usually at least about 12 amino acids in length, and may be as many as about 20 amino acids in length, up to substantially the length of the intact protein, may be used to identify and investigate parts of the protein important for function, or to raise antibodies directed against these regions.

With the availability of the protein or fragments thereof in large amounts, by employing an expression host, the protein may be isolated and purified in accordance with conventional ways. A lysate may be prepared of the expression host and the lysate purified using HPLC, exclusion chromatography, gel electrophoresis, affinity chromatography, or other purification technique. The purified protein will generally be at least about 80% pure, preferably at least about 90% pure, and may be up to and including 100% pure. Pure is intended to mean free of other proteins, as well as cellular debris.

The expressed GRAIL polypeptides are used for the production of antibodies, where short fragments provide for antibodies specific for the particular polypeptide, and larger fragments or the entire protein allow for the production of antibodies over the surface of the polypeptide. For example, antibodies may be targeted to the amino terminal region of the protein for purposes of cell staining. Antibodies may be raised to the wild-type or variant forms of GRAIL. Antibodies may be raised to isolated peptides corresponding to these domains, or to the native protein.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see *Monoclonal Antibodies: A Laboratory Manual,* Harlow and Lane eds., Cold Spring Harbor Laboratories, Cold Spring Harbor, N.Y., 1988. If desired, the mRNA encoding the heavy and light chains may be isolated and mutagenized by doning in *E. Coli,* and the heavy and light chains mixed to further enhance the affinity of the antibody. Alternatives to in vivo immunization as a method of raising antibodies include binding to phage "display" libraries, usually in conjunction with in vitro affinity maturation.

Antibodies specific for a GRAIL polypeptide may be used in staining or in immunoassays. Samples, as used herein, include biological fluids such as semen, blood, cerebrospinal fluid, tears, saliva, lymph, dialysis fluid and the like; organ or tissue culture derived fluids; and fluids extracted from physiological tissues. Also included in the term are derivatives and fractions of such fluids. The cells may be dissociated, in the case of solid tissues, or tissue sections may be analyzed. Alternatively a lysate of the cells may be prepared.

Diagnosis may be performed by a number of methods to determine the absence or presence or altered amounts of normal or abnormal GRAIL in patient cells. For example, detection may utilize staining of cells or histological sections, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a fluorescent compound, e.g. flourescein, rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc.

Other forms of mutations in GRAIL or its promoter or regulatory elements may be identified in "disease states" by sequence of the relevant gene segment. For example, a candidate polymorphism may be assayed for the ability of the encoded product to down-regulate IL-2 expression during T cell activation.

Diagnostic Uses of Anergy Associated Genes

The GRAIL and other anergy associated sequences provided herewith may be used to analyze a patient sample for the presence of polymorphisms or alterations in expression of sequences associated with T cell anergy; disease states; genetic predisposition to a disease state; and the like. The anergy associated sequences of Table I may be used in expression profiling of cells. Preferably a plurality of reference sequences, preferably comprising positive and negative control sequences, are distributed in an array for this purpose.

An array may include all or a subset of the reference sequences listed in Table 1. Usually such an array will include at least 20 different reference sequences, and may include all of the provided sequences. Arrays of interest may further comprise sequences, including polymorphisms, of other genetic sequences, particularly other sequences of interest for screening the responsiveness of T cells, e.g. IL-2, IL-2 receptor, etc. The oligonucleotide sequence on the array will usually be at least about 12 nt in length, may be the length of the provided polymorphic sequences, or may extend into the flanking regions to generate fragments of 100 to 200 nt in length.

Methods of producing large arrays of oligonucleotides are described in U.S. Pat. No. 5,134,854 (Pirrung et al.), and U.S. Pat. No. 5,445,934 (Fodor et al.) using light-directed synthesis techniques. Using a computer controlled system, a heterogeneous array of monomers is converted, through simultaneous coupling at a number of reaction sites, into a heterogeneous array of polymers. Alternatively, microarrays are generated by deposition of pre-synthesized oligonucleotides onto a solid substrate, for example as described in International Patent application WO 95/35505.

Microarrays can be scanned to detect hybridization of the labeled genome samples. Methods and devices for detecting fluorescenty marked targets on devices are known in the art Generally such detection devices include a microscope and light source for directing light at a substrate. A photon counter detects fluorescence from the substrate, while an x-y translation stage varies the location of the substrate. A confocal detection device that may be used in the subject methods is described in U.S. Pat. No. 5,631,734. A scanning laser microscope is described in Shalon et al. (1996) *Genome Res.* 6:639. A scan, using the appropriate excitation line, is performed for each fluorophore used. The digital images generated from the scan are then combined for subsequent analysis. For any particular array element, the ratio of the fluorescent signal from one Nucleic acid sample is compared to the fluorescent signal from the other Nucleic acid sample, and the relative signal intensity determined.

Methods for analyzing the data collected by fluorescence detection are known in the art. Data analysis includes the steps of determining fluorescent intensity as a function of substrate position from the data collected, removing outliers, i.e. data deviating from a predetermined statistical distribution, and calculating the relative binding affinity of the targets from the remaining data. The resulting data may be displayed as an image with the intensity in each region varying according to the binding affinity between targets and probes.

A number of methods are available for analyzing nucleic acids for the presence or quantity of a specific sequence, e.g. a disease associated polymorphism, changes in expression profile between a responsive and anergic cell, etc. Cells that are suspected of an anergic state may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. (1985) Science 239:487, and a review of techniques may be found in Sambrook, et al. Molecular Cloning: A Laboratory Manual, CSH Press 1989, pp.14.2–14.33. Alternatively, various methods are known in the art that utilize oligonucleotide ligation as a means of detecting polymorphisms, for examples see Riley et al. (1990) N.A.R. 18:2887–2890; and Delahunty et al. (1996) Am. J. Hum. Genet. 58:1239–1246.

A detectable label may be included in an amplification reaction. Suitable labels include fluorochromes, e.g. fluorescein isothiocyanate (FITC), rhodamine, Texas Red, phycoerythrin, allophycocyanin, 6carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods, and the sequence of bases compared to a wild-type GRAIL sequence. Hybridization with the variant sequence may also be used to determine its presence, by Southern blots, dot blots, etc. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Alternatively, where a polymorphism creates or destroys a recognition site for a restriction endonuclease, the sample is digested with that endonuclease, and the products size fractionated to determine whether the fragment was digested. Fractionation is performed by gel or capillary electrophoresis, particularly acrylamide or agarose gels.

Modulation of Gene Expression

The GRAIL genes, gene fragments, or the encoded protein or protein fragments are useful in gene therapy to treat disorders associated with GRAIL defects; to down-regulate the responsiveness of T cells, etc. Expression vectors may be used to introduce the GRAIL gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The gene or GRAIL protein may be introduced into tissues or host cells by any number of routes, including viral infection, microinjection, or fusion of vesicles. Jet injection may also be used for intramuscular administration, as described by Furth et al. (1992) *Anal Biochem* 205:365–368. The DNA maybe coated onto gold microparticles, and delivered intradermally by a particle bombardment device, or "gene gun" as described in the literature (see, for example, Tang et al. (1992) *Nature* 356:152–154), where gold microprojectiles are coated with the GRAIL protein or DNA, then bombarded into skin cells.

Antisense molecules can be used to down-regulate expression of GRAIL in cells. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like.

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art. Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Genetically Altered Cell or Animal Models for Grail Function

The subject nucleic acids can be used to generate transgenic animals or site specific gene modifications in cell lines. Transgenic animals may be made through homologous recombination, where the normal Grail locus is altered. Alternatively, a nucleic acid construct is randomly integrated into the genome. Vectors for stable integration include plasmids, retroviruses and other animal viruses, YACs, and the like.

The modified cells or animals are useful in the study of Grail function and regulation. In one embodiment of the invention, the GRAIL coding sequence is stably or transiently introduced into T cells, e.g. splenocytes, T cell hybridomas, etc. for determining the role of GRAIL in regulation of T cell responsiveness.

In another embodiment, a series of small deletions and/or substitutions are made in the Grail gene to determine the role of different domains in anergy induction or maintenance, etc. Of interest are the use of GRAIL to construct transgenic animal models for immune disorders, e.g. autoimmune diseases and the like, where expression of GRAIL is specifically reduced or absent, e.g. in T cells, etc. Specific constructs of interest include anti-sense GRAIL, which will block GRAIL expression, expression of dominant negative GRAIL mutations, etc. A detectable marker, such as lac Z may be introduced into the Grail locus, where upregulation of Grail expression will result in an easily detected change in phenotype.

One may also provide for expression of the Grail gene or variants thereof in cells or tissues where it is not normally expressed or at abnormal times of development. In addition, by providing expression of GRAIL protein in cells in which it is not normally produced, one can induce changes in cell behavior, e.g. through GRAIL mediated signaling modulation.

DNA constructs for homologous recombination will comprise at least a portion of the Grail gene with the desired genetic modification, and will include regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keyed et al. (1990) *Methods in Enzymology* 185:527–537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies, drug screening, etc., e.g. to determine the effect of a candidate drug on T cell mediated immune responses, etc.

In vitro Models For Grail Function

Drug screening may be performed to determine the effect of a candidate agent on induction and/or maintenance of anergy, using an in vitro model, a genetically altered cell or animal, or purified GRAIL protein. One can identify ligands or substrates that bind to, modulate or mimic the action of GRAIL. Areas of investigation include the treatment of T cell mediated immune disorders, and "cancer specific" T cells (for example, see Lee et al. (1999) Nat. Med. 5:677–685); etc. Also of interest is the screening of agents through determining the effect on multiple anergy associated sequences, e.g. the sequences set forth in Table I. A panel or array of polynucleotides or polypeptides may be used to determine changes in gene expression, binding to polypeptides, etc.

In another screening method, two hybrid analysis is performed to characterize proteins that interact with GRAIL. For example, the putative RING domain may be used as "bait" in order to characterize sequences from a library that are capable of interaction with GRAIL.

Agents that reverse GRAIL or anergy related sequence function may act to enhance immune reactivity, for example against tumor cells, while agents that enhance GRAIL or anergy related sequence are expected to reduce the responsiveness of affected T cells. Of particular interest are screening assays for agents that have a low toxicity for human cells. A wide variety of assays may be used for this purpose, including labeled in vitro protein-protein binding assays, electrophoretic mobility shift assays, immunoassays for protein binding, and the like. The purified protein may also be used for determination of three-dimensional crystal structure, which can be used for modeling intermolecular interactions.

The term "agent" as used herein describes any molecule, e.g. protein or pharmaceutical, with the capability of altering or mimicking the physiological function of Grail. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

The compounds having the desired pharmacological activity may be administered in a physiologically acceptable carrier to a host for treatment of autoimmune disease, to enhance immune response to tumor cells, etc. The inhibitory agents may be administered in a variety of ways, orally, topically, parenterally e.g. subcutaneously, intraperitoneally, by viral infection, intravascularly, etc. Topical treatments are of particular interest. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

Experimental

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXAMPLE 1

Characterization of Anergy Associated Genes

Materials and Methods

Cell Lines. The murine T cell clone 11.3.7 was isolated from DBA/2 mice immunized with whole sperm whale myoglobin (SWM). This CD4+ T cell clone recognized amino acids 110–121 of SWM in the context of a mixed class II haplotype ($E\alpha^d A\beta^d$) which is present at low levels on DBA/2 APCs. 11.3.7 cells were maintained in culture using irradiated DBA/2 splenocytes as APCs and 10 $\mu$M 110–121 SWM according to established protocols (Gaur, G. 1996. Cloning of Murine T Cells. *Methods*. 9:411–415). 11.3.7 cells were restimulated on a 10–14 day cycle. The RT 7.7 fibroblast cell-line is transfected with the mixed isotype ($E\alpha^d A\alpha^d$) MHC class II gene. The RT 7.7 line expressed no B7 on its cell surface as shown by FACS analysis with anti-B7-1 and anti-B7-2 antibodies. The B7(+) (B7-expressing) RT 7.7 line was generated by stable transfection of a B7-1 cDNA construct pL444-mB7. The construct was linearized and electroporated according to established protocols. Stably transfected B7(+) RT 7.7 cells were selected in 1 mg/ml G418 and screened by FACS analysis with an anti-B7-1, PE-labeled antibody (Pharmingen).

Anergy Assays. Resting 11.3.7 T cells were purified on a Lympholyte M (Cedarlane Labs) gradient and washed three times with 1×PBS. Costimulatory incompetent APCs, (B7 negative RT 7.7 fibroblasts), were irradiated at 3000 rads prior to use in antigen-induced anergy cultures. $6 \times 10^6$ T cells were mixed with $6 \times 10^6$ B7 negative RT7.7 APCs in 20 mls of culture media. 10 $\mu$M SWM 110–121 peptide was added to the anergic cultures to activate signal one (resting control cultures did not receive antigen). Full antigen activation was achieved in similar cultures in which costimulatory competent, B7 positive RT7.7 APCs, were used. For ionomycin-induced anergy, $2 \times 10^6$ 11.3.7 T cells were incubated with 1.5 $\mu$M ionomycin (Calbiochem). For full activation, 1 $\mu$g/ml PMA was added to the cultures.

At selected time intervals, aliquots of both cultures were harvested, pelleted, and washed twice before adding 10 $\mu$l of anti-CD4 microbeads (Millenyl Biotech) to separate CD4+ T cells from the RT 7.7 fibroblast APCs, according to the manufacturer's protocol. As determined by flow cytometry, greater than 95% purity was routinely achieved. To test for the anergic phenotype, $50 \times 10^4$ T cells/well were then cultured with irradiated DBA/2 splenocytes and various concentrations of peptide in a 96 well plate. In selected cultures, murine rIL-2 (Genzyme) was added at 5 Units/ml during the restimulation period, to test the viability of the anergized T cells. After 48 hours of culture, the cells were pulsed for 18 hours with 3H-Thymidine, then harvested and counted.

Differential Display. RNA samples obtained from 11.3.7 T cells treated under resting, activating, or anergic conditions using a Qiagen isolation kit were subjected to reverse transcription and differential display using the entire differential display system designed by Genomyx (Foster City, Calif.). cDNAs were reverse transcribed using ten different 3' oligo dT primers (according to the manufacturer's protocol) from resting, anergic, and activated RNA samples. Eighteen 5' primers, included in the Genomyx kit, were used to amplify the ten cDNA templates (using the appropriate 3' primers) for a total of 180 different primer combinations for each T cell phenotype (anergic, resting, or activated). Duplicate PCR reactions were performed for selected primer combinations to verify differentially expressed bands. Templates were amplified in the presence of $^{35}$S-dATP for PCR product detection and after 40 cycles of amplification, the samples were run on 4.5% acrlamide gels using the Genomyx gel apparatus and exposed to X-ray film. cDNA fragments that appeared to be present at higher levels in anergic lanes were excised from the gel and re-amplified to achieve sufficient DNA levels for cloning. These selected cDNA fragments were cloned using the TA cloning kit (Invitrogen), sequenced using standard protocols and analyzed as described below for quantitative levels of mRNA expression. Those candidate anergy genes that were reproducibly expressed at higher levels in the anergic cells were then studied for potential sequence homologies using the NCBI Blast system.

"Real-time" Quantitative PCR. Total RNA was isolated as described above and 0.5 $\mu$g was reversed transcribed using the TaqMan reverse transcription reagent kit (PE Applied Biosystems) according to recommended protocols. Subsequently, 1 $\mu$l aliquots of cDNA (equivalent to 5 ng of input RNA) were amplified in separate reactions with primer pairs and fluorescent probe sets specific for GAPDH (to generate a standard curve to control for input cDNA amounts) and for target mRNAs identified in the differential display screen. Resting, activated and anergic RNA samples were also amplified using specific primers and a probe for IL-2. Standard cycling conditions and PCR protocols were used for the ABI PRISM 7700 Sequence Detection System (PE Applied Biosystems). Primers and fluorogenic probes for target mRNAs were designed using the Primer Express software (Perkin Elmer, Norwalk, Conn.) according to specific requirements for the ABI PRISM 7700 Sequence Detection System. Probes and primer sets specific for GAPDH and target mRNAs were purchased from PE Applied Biosystems.

Using the relative standard curve method described in protocols provided by ABI, changes in target RNA expression for the different ddPCR cDNA clones and IL-2 were calculated as fold increases over resting cells. To control for input RNA amounts, the relative amount of GAPDH RNA was determined for each sample (resting, anergic, and activated) from a standard curve generated for GAPDH. Then, the target amount of a particular ddPCR cDNA was divided by the GAPDH amount to obtain a normalized value. Standard curves for both target genes and GAPDH were determined by quantitative PCR reactions using serial dilutions of known amounts of cDNA or plasmids containing relevant inserts.

Results

The kinetics of anergy induction. Both an antigen-induced, and an ionomycin-induced anergy system were used to determine the kinetics of anergy induction. This allows for the analysis of differential gene expression during the inductive phase of anergy. In the antigen-induced anergy system, B7 negative RT 7.7 fibroblasts, transfected with the appropriate MHC class II molecule, were used as APCs to present a peptide of sperm whale myoglobin (SWM 110–121) to the CD4+ T cell clone 11.3.7 to induce the anergic state. The ionomycin-induced anergy system) used the same T cell clone cultured in the presence of 1.5 $\mu$M ionomycin. In both systems, a state of functional unresponsiveness was seen in response to restimulation with antigen and costimulatory competent B7 positive APCs (FIG. 1).

To study potential changes in gene expression in the induction of T cell anergy, we determined the minimum duration of signaling through the TCR (signal one) necessary for the development of the anergic phenotype in the antigen-induced anergy system. At timed intervals, T cells were removed from the anergy or control cultures, and their proliferative responses were analyzed following restimulation with irradiated DBA/2 splenocytes and serial concentrations of SWM 110–121 peptide. As shown in FIG. 1A, following one hour of culture with antigen in the absence of costimulation, T cells from the anergy cultures responded as well as resting T cells to restimulation with professional APCs and antigen. However, by 3–4 hours of culture, anergized 11.3.7 T cells had a dramatically reduced proliferative response to restimulation, when compared to the resting control. At 6 hours, the anergic phenotype was complete, and was retained in anergized T cells for 24 hours or more (FIG. 1A). Anergized T cells remained viable for at least 24 hours; addition of IL-2 to the restimulation cultures induced as strong a proliferative response in the anergized T cells as it did in the resting, control T cells (FIG. 1C). Using this system, engagement of the TCR (in the absence of costimulation), for as little as 3–6 hours, resulted in a profound state of non-responsiveness.

Previous studies have demonstrated that treatment of CD4+ T cells with the calcium ionophore, ionomycin, in the absence of PMA (costimulation), effectively induced T cell anergy. To determine whether ionomycin-induced anergy followed similar kinetics to the model described above, 11.3.7 T cells were incubated with 1.5 $\mu$M ionomycin for 1, 6 and 24 hours and assayed for their proliferative capacity in restimulation cultures with fully competent DBA/2 splenocytes and SWM 110–121 peptide. Similar to the antigen-induced system, a one hour incubation of the 11.3.7 T cells with ionomycin did not induce a state of functional unresponsiveness (FIG. 1B). however by 6 hours incubation, ionomycin-induced anergy was complete. The observed unresponsiveness in the ionomycin-induced anergy cultures could also be overcome by the addition of IL-2 to the restimulation cultures (FIG. 1D) indicating that the unresponsive T cells were viable. Thus, ionomycin-induced T cell anergy demonstrated similar kinetics to the antigen-induced model.

IL-2 mRNA expression during anergy induction. The lack of IL-2 mRNA transcription in anergic T cells, following restimulation with competent APCs and antigen, has been well characterized. However, IL-2 message levels in the early phase of anergy induction in the models described above have not been determined. Using quantitative PCR, we determined the relative levels of IL-2 message in 11.3.7 T cells following 4 hours of stimulation under resting, activating or anergizing conditions in both anergy induction systems. IL-2 message levels were much lower ($\leq 2\%$) in anergic 11.3.7 cells stimulated with antigen presented by B7 negative APCs (anergic), when compared to cells activated with antigen presented by B7 positive APCs (activated) (FIG. 2). Similarly, IL-2 mRNA levels were dramatically reduced ($\leq 0.5\%$) in 11.3.7 T cells stimulated for 4 hours with ionomycin, when compared to cells which were activated with both PMA and ionomycin (FIG. 2). These data indicate that anergy induction coincides with greatly reduced transcription of IL-2 message.

Use of differential display to examine changes in gene expression during antigen-induced T cell anergy. Previous studies examined "mechanisms" of anergy after extended periods ($\geq 24$ hours) of TCR signaling. Our analysis of the two different models of T cell anergy induction described above, demonstrated that the anergic phenotype was complete within 4–6 hours of activation in both systems (FIG. 1). Thus, this time period seemed to be appropriate to study potential differential gene expression during the induction of T cell anergy.

Differential display (ddPCR) was used to compare differences in mRNA expression in 11.3.7 T cells following antigen-induced anergy for four hours, to T cells from both resting and activated cultures. The identical antigen-induced anergy system that was used for the determination of the kinetics of anergy induction was used to generate RNA samples for ddPCR analysis. RNA samples for ddPCR were analyzed from cultured cells whose activation status (anergic, resting, or activated) was verified by restimulation and proliferation assays.

Several ddPCR cDNA fragments that showed increased expression in anergic T cells, relative to activated or resting T cells, were identified as "candidate" anergy genes whose expression was upregulated in the anergic state. ddPCR fragments expressed at higher levels in activated and/or resting cells have not been further characterized. A ddPCR gel showing increased expression of a cDNA fragment, 19.9.6-3, (arrowhead) in the anergic lanes relative to resting and activated lanes. Additional bands showing specific up-regulation in anergic lanes were classified as candidate anergy genes. Those cDNAs that were reproducibly expressed at higher levels in the anergy lanes in replicate ddPCR assays, were excised from the gels, re-amplified and cloned into the TA cloning vectors for further characterization.

Verification and quantitation of differential expression by "Real-Time" PCR. Because differential display results are largely qualitative, it was important to verify ddPCR results using a precise method of quantifying and comparing RNA levels of candidate anergy genes. Initial Northern blotting experiments using ddPCR products as probes verified the differential expression of several of the identified clones, including 6.5.2-4, 19.9.6-3, 9.3.1-2, and 1-4. However because of increased sensitivity and reproducibility, the ABI PRISM 7700 Sequence Detection System for "real-time" quantitative PCR was utilized in subsequent experiments to precisely quantify changes in gene expression during T cell anergy induction.

Figure 3B:
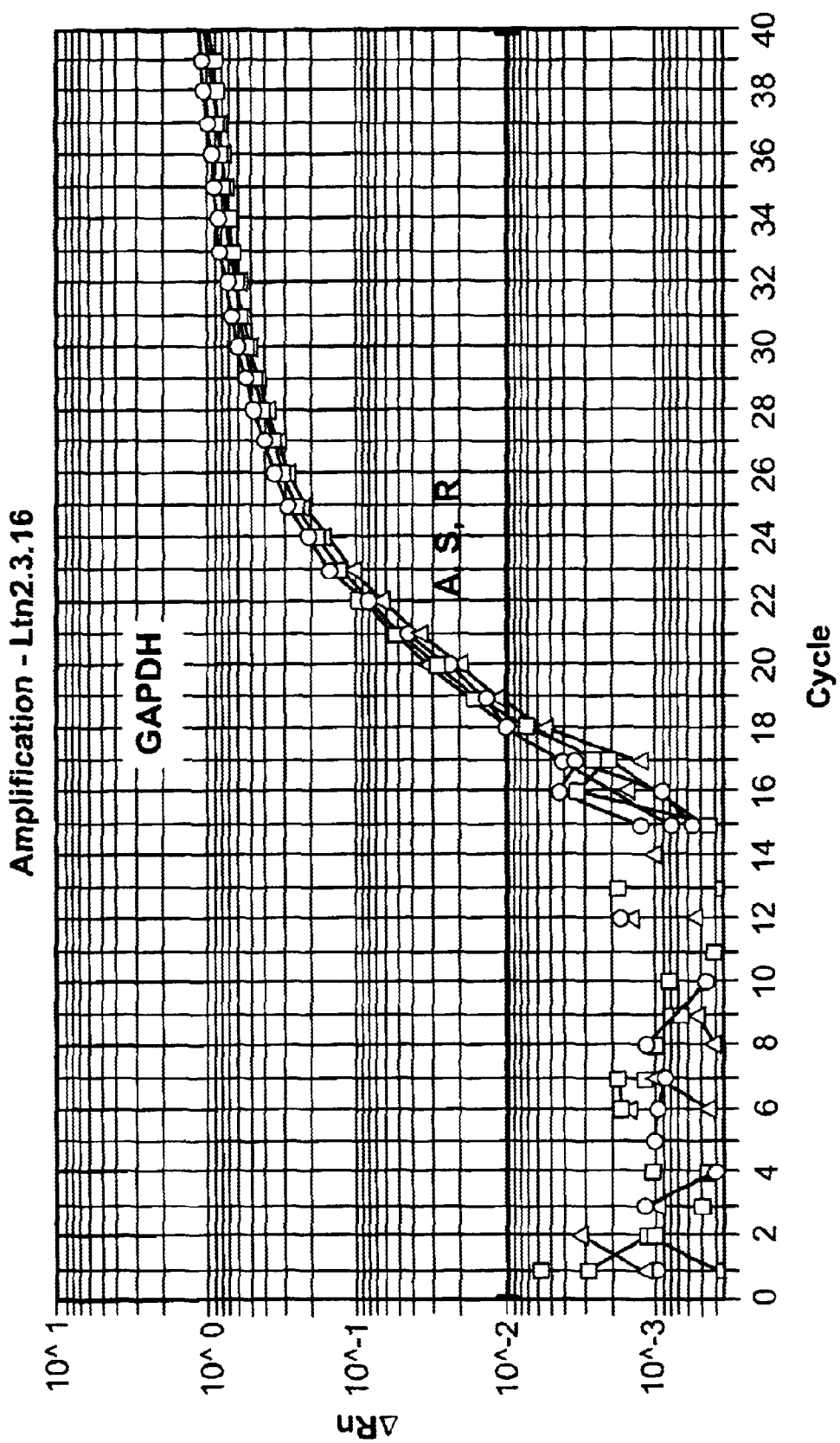

Specific primer pairs and fluorogenic probes, designed based on the sequences of the different ddPCR cDNA clones, were used to amplify cDNA samples from resting, activated and anergic T cells. FIG. 3 is a representative amplification plot from a "real-time" quantitative PCR experiment, showing the differential expression of cDNA clone 6.5.2-4 (lymphotactin) from an antigen-induced anergy assay. A shift to the left of the amplification curve for the anergic T cell RNA sample (A) using 6.5.2-4 specific primers, indicates an increased amount of 6.5.2-4 message, relative to activated (S) and resting (R) T cells (FIG. 3A). Amplification of identical RNA samples in separate reactions with a GAPDH-specific primer and probe set, indicated equivalent levels of GAPDH expression and, therefore, equal input of total RNA into anergic (A), activated (S) and resting (R) PCR reactions (FIG. 3B).

The relative expression of target mRNAs (identified in the ddPCR screen) in resting, anergic and activated T cells was analyzed using this PCR system and the relative standard curve method for quantification (described in Materials and Methods). As shown by data presented in Table I (top), increased gene expression in antigen-induced anergic T cells (reflected by the anergic:activated ratio) ranged from 1.5 fold (9.3.1-2) to 8.0 fold (6.5.2-4). For each ddPCR product, similar differences were observed in multiple quantitative PCR experiments. These PCR experiments confirmed the differential expression patterns of cDNAs identified by ddPCR, and precisely quantitated the relative differences in expression between resting, activated and anergic 11.3-7 T cells. Additionally, these differences were similar to those observed by Northern analysis of anergy gene expression.

Quantitative PCR was then used to determine the relative expression levels of the candidate anergy genes in the ionomycin-induced anergy system. For two of the cDNAs, 1-4 and A9.5.7-4, the ratio of anergic to activated mRNA expression was similar between the two models of anergy (Table I and FIG. 4). For example, the 3.1-fold induction of the 1-4 message in antigen-induced anergic cells (relative to activated cells) was similar to the 3.3-fold induction observed in the ionomycin-induced anergy model. Ionomycin treatment, which lead to T cell unresponsiveness with similar kinetics to the antigen-induced anergy system (FIG. 1), induced up-regulation of two of the candidate anergy genes, A9.5.7-4 and 1-4, but did not lead to differential expression of the other three candidate genes, 19.9.6-3, 6.5.2-4, and 9.3.1-2, when compared to the level in the PMA and ionomycin activated T cells. For example, the 8.0-fold induction of the 65.2-4 message in antigen-induced anergic cells (relative to activated cells) was not similar to the 0.84-fold difference observed in the ionomycin model (Table I and FIG. 4).

Sequencing of ddPCR anergy genes and nucleotide sequence homologies. ddPCR fragments which were differentially expressed in duplicate PCR amplifications and whose increased expression was confirmed by quantitative PCR in the antigen-induced anergy system were re-amplified, cloned into the TA cloning vector, sequenced, and analyzed for nucleotide sequence homology by NCBI Blast searches. The five ddPCR cDNA clones whose expression was increased in anergic T cells, relative to resting and activated T cells, are listed in Table II. The most significant sequence homologies identified for each ddPCR product from GenBank analysis are indicated.

Clone 19.9.6-3 had a high sequence homology with two members of the nuclear orphan receptor family of transcription factors: murine Nurr2 (a splice variant of the Nurr1 message) and rat RNR-1 (rat homologue of murine Nurr-1). Another clone, 6.5.2-4, had 99% sequence identity to murine lymphotactin, a recently identified chemokine which has chemotactic activity for lymphocytes and was previously identified as a gene expressed in anergic T cells. Clone A9.5.7-4 had 92% sequence identity to the 3'-UTR region of the human CBL-b gene, a protein which is thought to play an important role in the negative regulation of immune receptor signal transduction. Clone 9.3.1-2 had a high level of homology to rat OX44, a tetraspanin family member and lymphocyte surface marker. The "unknown" ddPCR clone 1-4 had no significant nucleotide sequence homologies upon BLAST searching.

TABLE I

Relative mRNA expression levels in anergic, resting, or activated 11.3.7 T cells

| Antigen anergy | Anergic Ag, B7-APC | Activated Ag, B7 + APC | anergic:activated ratio |
| --- | --- | --- | --- |
| 9.3.1–2 | 2.9 | 1.9 | 1.5 |
| 19.9.6–3 | 41.6 | 14.8 | 2.8 |
| 6.5.2–4 | 718.2 | 89.3 | 8.0 |
| A9.5.7–4 | 6.0 | 2.9 | 2.1 |
| 1–4 | 6.3 | 2.0 | 3.1 |

| Ionomycin anergy | Anergic + ion | Activated + PMA/ion | anergic:activated ratio |
| --- | --- | --- | --- |
| 9.3.1–2 | 10.2 | 14.3 | 0.71 |
| 19.9.6–3 | 21.7 | 20.2 | 1.1 |
| 6.5.2–4 | 153 | 183 | 0.84 |
| A9.5.7–4 | 11.0 | 8.0 | 1.4 |
| 1–4 | 4.0 | 1.2 | 3.3 |

[a]Expression of ddPCR cDNAs in activated and anergic T cells (compared to resting) as determined by "real-time" quantitative PCR. The relative quantity of target mRNAS was determined by quantitative PCR (described in Materials and Methods) using ddPCR fragment-specific primer pairs and fluorogenic probes. Data from the antigen-induced anergy model is presented in the upper half of the table, while data fromthe ionomycin-induced model is in the lower half. Using the relative standard curve method, changes in expression for the different ddPCR clones were calculated as fold increases over expression in resting T cells which was set to 1.0. To control for input RNA levels, the relative amount of a particular target cDNA was divided by the relative amount of GAPDH message to obtain a normalized value.

TABLE II cDNA clones differentially expressed in anergic T cells

| Fragment Name | Expression | Sequence Homology |
| --- | --- | --- |
| 9.3.1–2 | A s r | Rat leukocyte antigen MRC-OX44 mRNA, 88% identity |
| 19.9.6–3 | A s | Mus musculus mRNA for Nurr2, 98% identity<br>Rat nuclear receptor (RNR-1) mRNA, 94% identity |
| 6.5.2–4 | A s | SCM-1 motif murine lymphotactin mRNA, 99% identity |

TABLE II-continued cDNA clones differentially expressed in anergic T cells

| Fragment Name | Expression | Sequence Homology |
|---|---|---|
| A9.5.7–4 | A s r | Human cbl-b mRNA, 92% identity |
| 1–4 | A s r | NONE |

[a]Differential display cDNA clones upregulated in anergic T cells relative to resting and activated cells. ddPCR cDNA fragments were excised from the differential display gel, cloned, sequenced and analyzed for potential sequence homologies using BLAST searches. The first column indicates the fragment name (as determined by the specific PCR primer pair combination used). The second column shows theexpression pattern of a particular cDNA clone determined by differential display: 'A' indicates expression in anergic cells; 'R' indicates expression in resting cells; and 'S' indicates expression in activated cells. Uppercase letters indicate higher levels of expression relative to other activation states. The third column shows the most significant sequence homology (and the % identity) ofparticular ddPCR clones. "Unknown" indicates that the ddPCR fragment did not have any significant sequence homology to any known gene.

Positive (activation) and negative (anergy) responses in T cells could be due to either differences in signal quantity (activation leads to more intense TCR signals) or signal quality (whereby signals for anergy induction could be a subset of signals required for activation, or vice versa). Recent data suggest that there may be differences in the quantity of signals generated in anergic versus activated T cells: (e.g.) the reduced ERK and JNK activation (Ras pathway) observed in anergic relative to activated T cells. Additionally, anergic T cells have been characterized by diminished recruitment of the kinases lck and fyn to the T cell receptor, reduced phosphorylation of TCR ITAM motifs, and a subsequent reduction in the activation of ZAP70.

Although several differences in intercellular signaling events have been observed in anergic T cells (which supports the signal quantity model), few studies have focused on the possibility that a unique set of genes may be quantitatively overexpressed during the induction of anergy. The studies described herein investigated whether "anergy-specific" genes were expressed during the induction of anergy in CD4+ T cells, or whether anergy was the result of the induction of a qualitatively or quantitatively different subset of genes than that required for full activation. The identification of the negative transcriptional regulator of IL-2, Nil-2-a, which, by less qualitative analysis, seemed to be expressed exclusively in anergic T cells within 6 hours of TCR signaling and other studies demonstrating cis-dominant negative repression of the IL-2 promoter in anergized T cells support the idea that there may be unique genes whose expression is increased during anergy induction. The recent identification of increased GRP-1 (general receptor of phosphoinosifides) expression in anergic T cells by ddPCR (≧24 hours after anergizing signal) indicated that specific genetic changes may be involved in maintaining the unresponsive phenotype.

In this study early changes in gene expression that are involved in the initial development of the anergic state are characterized. Using the technique of differential display, five cDNAs were identified (including one corresponding to the gene for lymphotactin) which were expressed at higher levels in antigen-induced anergic T cells, when compared to activated or resting T cells. No genes were identified that were expressed uniquely in the state of T cell anergy.

Clone 6.5.2-4 (homologous to lymphotactin) was expressed at 8-fold higher levels in antigen-induced anergic T cells (relative to activated). This observation is consistent with the results of Hautamaa et al., 1997 who cloned murine lymphotactin from a cDNA library produced from an unresponsive Th1 cell clone and demonstrated that lymphotactin mRNA expression was maximal in TCR-stimulated cells not receiving CD28 costimulation.

Another clone, 9.3.1-2, had homology to the rat OX44 gene, and may represent the murine OX44 homologue, CD53. This cDNA was expressed at a slightly higher level in the antigen-induced but not ionomycin-induced anergic T cells when compared to activated T cells (1.5-fold). CD53 is a pan-leukocyte member of the tetraspanin (trans-membrane 4) family of receptors for which little is known concerning potential signaling functions in lymphocytes. There have been reports that CD53 expression might be induced by T cell receptor engagement during thymic selection and that CD53 was associated non-covalently with several other membrane proteins involved in cellular activation.

Although the 19.9.6-3 cDNA showed 2–3-fold increased expression in the antigen-induced anergic versus activated T cells, it was not differentially expressed in the ionomycin-induced anergy system. This ddPCR fragment had high homology to Nurr2, and the rat nuclear receptor cDNA (RNR-1, rat homologue of murine Nurr1) both of which belong to the Nur77 group of nuclear receptor transcription factors. Nurr2 is a recently identified splice variant of Nurr1. Recent evidence indicates that members of the Nur77 nuclear orphan receptor family of transcription factors (which includes Nurr1 and Nurr2) may have direct roles in TCR signaling. For example, TCR-induced apoptosis is blocked by a dominant-negative Nur77 protein and inhibition of Nur77/Nurr1 leads to the inefficient clonal deletion of self-reactive T cells. Interestingly, transient transfection experiments suggested that Nurr2 may act as a negative transcription factor.

Clone A9.5.7-4, which was expressed at higher levels in anergic T cells from both systems, (Table II), has 92% identity to the 3'-UTR sequence of the human CBL-b mRNA. Interestingly, CBL-b belongs to the CBL family of adapter proteins that can be phosphorylated and are involved in positive or negative regulation of various signaling pathways through interactions with specific kinases. Although previous data have suggested that some members of the CBL family may act as negative signaling regulators, a recent study indicated that CBL-b interacts with ZAP-70 and acted as a positive signal in T cell activation.

More recent gene knockout studies have shown that CBL-b acts as a negative regulator of lymphocyte activation which controls the CD28 dependence of T cell activation. In two separate studies, T cells from CBL-b –/– mice did not require CD28 costimulation for activation and IL-2 production. Although other TCR signaling pathways such as the MAPK pathway were unaffected, the activation of Vav (a guanidine nucleotide exchange factor) was enhanced in CBL-b –/– mice, suggesting a normal role for CBL-b in inhibiting Vav activation. More interestingly, in both studies CBL-b –/– mice either had spontaneous autoimmune disease or were more susceptible to induction of an autoimmune disease (EAE). These observations support the hypothesis that CBL-b is involved in holding self-reactive T cells in an anergic/tolerant state. Increased expression of CBL-b in anergic T cells (which have received TCR signaling in the absence of costimulaton) may prevent Vav activation even in response to full activation through both the TCR and CD28.

Upon comparison of the two anergy models (antigen vs. ionomycin-induced), three of the five identified anergy genes were not equivalently upregulated. This discrepancy may reflect the different molecular mechanisms which are involved in the induction of anergy by either ionomycin or TCR stimulation (in the absence of costimulation). Ionomycin induction of increased intracellular $Ca^{2+}$ levels, represents only a subset of the signals which are generated through TCR signaling. Increased expression of these anergy genes (9.3.1-2, 19.9.6-3, 6.5.2-4) may therefore occur through a TCR-induced signal, which does not involve increased calcium flux (ie. MAPK pathway). It is interesting that the other energy genes, 1-4 and A9.5.7-4 are expressed at a higher level in both ionomycin-induced and antigen-induced anergic T cells. Perhaps transcription of these genes is induced by a $Ca^{2+}$-dependent pathway involving NFAT activation. Of the five identified candidate genes, 1-4 and A9.5.7-4 show a direct functional roles in anergy induction, because their upregulation coincides with the unresponsive phenotype in two different systems.

In summary, it is found that T cell anergy was induced rapidly and with similar kinetics in both systems, within 4–6 hours of the anergy induction signal. In both models, anergy induction was followed by a marked reduction in IL-2 mRNA expression. Based on the initial kinetic studies, differential display was used to identify cDNAs that were expressed at higher levels during this period of early anergy induction in the antigen-induced anergy system, and was then compared the "candidate" anergy gene expression in the ionomycin-induced anergy system. The data suggest that anergy induction is not simply a "default" state, characterized by the absence of full activating signals provided by costimulatory interactions. Rather, the induction of T cell anergy is an active process involving the induction of certain genes, resulting in differences in signal quantity and possibly quality.

EXAMPLE 2
Functional Characterization of GRAIL

In order to determine the biological effects of GRAIL expression, T cells were transduced or transfected with GRAIL expression constructs, then stimulated, and the response monitored.

In a first example, shown in FIG. 5A, ConA preactivated DBA/2 mouse splenocytes were co-transfected with pRL-null (renilla luciferase) as a transfection control; a reporter plasmid containing the firefly luciferase gene under the control of the minimal IL-2 promoter (pIL-2pGL2); and the pREP4 expression controls containing either no insert (control) or the GRAIL cDNA. Two hours post-transfection, cells were stimulated with PMA/Ionomycin for 6 hours, after which renilla luciferase and firefly luciferase levels were measured. Shown in FIG. 5A are the results of three independent transfection experiments. For each, firefly luciferase values were divided by renilla luciferase values (to control for transfection efficiency) and the level of unduction in control transfected cells was set to one. It can be seen the co-transfection with GRAIL (1-4) significantly diminished the IL-2 response to ionomycin and PMA.

In a second example, a T cell hybridoma cell line was stably transfected with an retroviral expression vector for GRAIL (shown in FIG. 5B, the columns marked MBP Gol and Col2 Gol). The expression of IL-2 in the hybridoma cells in response to ionomycin and PMA was measured by ELISA. Again, it can be seen that there is a marked reduction in the IL-2 response in the cells constitutively expressing GRAIL.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

---

What is claimed is:

1. An isolated nucleic acid molecule other than a naturally occurring chromosome comprising a sequence encoding the amino acid sequence set forth in SEQ ID NO:8.

2. An isolated nucleic acid molecule according to claim 1, wherein said nucleic acid comprises the nucleotide sequence set forth in SEQ ID NO:7.

3. An expression cassette comprising a transcriptional initiation region functional in an expression host, a nudeic acid having a sequence of the isolated nucleic acid according to claim 1 under the transcriptional regulation of said transcriptional initiation region, and a transcriptional termination region functional in said expression host.

4. A cell comprising an expression cassette according to claim 3 as part of an extrachromosomal element or integrated into the genome of a host cell as a result of introduction of said expression cassette into said host cell, and the cellular progeny of said host cell.

5. A cell comprising a nudeic acid according to claim 1 as part of an extrachromosomal element or integrated into the genome of a host cell as a result of introduction of said expression cassette into said host cell, and the cellular progeny of said host cell.

6. A method for producing GRAIL protein, said method comprising: growing a cell according to claim 4, whereby said GRAIL protein is expressed; and isolating said GRIL protein free of other proteins.

* * * * *

SEQUENCE LISTING

<160> NUMBER OF SEQ ID NOS: 8

<210> SEQ ID NO 1
<211> LENGTH: 239
<212> TYPE: DNA
<213> ORGANISM: Mus musculus

<400> SEQUENCE: 1

| | | | | | |
|---|---|---|---|---|---|
| ttgagtttag | ccccaaatac | tacaaaaaag | aggtccaagt | ttaaatgtta | ctctcctaac | 60 |
| aactgtcaaa | tcaatttcta | gcctctaaat | cttgctactt | ccactccaca | aagtcacata | 120 |
| agagagaagc | tgatggaaat | ttttgagtcc | cattcattag | ataattgaca | tactcagttt | 180 |
| cctttgaac | acagtccttg | gtaataggaa | tcatacagaa | atcttttatt | tctggaaaa | 239 |

<210> SEQ ID NO 2
<211> LENGTH: 260
<212> TYPE: DNA
<213> ORGANISM: Mus musculus

<400> SEQUENCE: 2

| | | | | | |
|---|---|---|---|---|---|
| ggattttggc | tccggggcat | cctggattta | gaaaacggac | agcacacagt | acagtggtat | 60 |
| aaacttttta | ttatcagttc | aaaatcagtt | tgttgttcag | aagaaagatt | gctaatgtat | 120 |

```
gatgggaagt gtttggccat gcttgcttgt tggcagttaa gacaaatgta acacacacac    180
acacacacac acacacacac acacatgaga tgagtcactg ccttctatgg ccttctatgg    240
tgtacgacag ttagagatgc                                                260
```

<210> SEQ ID NO 3
<211> LENGTH: 500
<212> TYPE: DNA
<213> ORGANISM: Mus musculus
<400> SEQUENCE: 3

```
cccagcaaga cctcagccat gagacttctc ctcctgactt tcctgggagt ctgctgcctc     60
accccatggg ttgtggaagg tgtggggact gaagtcctag aagagagtag ctgtgtgaac    120
ttacaaaccc agcggctgcc agttcaaaaa atcaagacct atatcatctg ggagggggcc    180
atgagagctg taatttttgt caccaaacga ggactaaaaa tttgtgctga tccagaaccc    240
aaatgggtga agcagcgat  caagactgtg gatggcaggg ccagtaccag aaagaacatg    300
gctgaaactg ttcccacagg agcccagagg tccaccagca cagcagtaac cctgactggg    360
taacagcctc caggacaatg tttcctcact cgttaagcag ctcatctcag ttcccaaacc    420
cattgcacaa atacttattt ttattttta cgacattcac attcatttca aatgttataa    480
gtaataaata tttattattg                                                500
```

<210> SEQ ID NO 4
<211> LENGTH: 264
<212> TYPE: DNA
<213> ORGANISM: Mus musculus
<400> SEQUENCE: 4

```
agccgaatta tacaatttca cacaggaatg gtagtctgaa ggtcctgatt tttcagtgtt     60
tcaaactaat gcagaaagaa aaggaaaat  gtgtgtggta ttgtcttcac tactgagtct    120
tttctttggg aaccatcact gttgagaggt gggggaaaac ctgaatgtaa aaagcattta    180
tttgtcaata aactgccttt tgtaaaaaaa agccctatag tgagtcgtat tacaagccga    240
ttctgcgaaa ttccatcaca ctaa                                           264
```

<210> SEQ ID NO 5
<211> LENGTH: 2145
<212> TYPE: DNA
<213> ORGANISM: Mus musculus
<220> FEATURE:
<221> NAME/KEY: CDS
<222> LOCATION: (358)...(1641)

<400> SEQUENCE: 5

```
caagcgatta agttgggtaa cgccaggttt tcccagtcac gacggttgta aaacgacggg     60
ccagtaattg taatacgacc tcactatagg gcgaattggg tacacttacc tggtaccccca   120 cccgggtgga aatcgatgg  gcccgcggcc gctctagaag tactctcgag aagcttttg    180 aattcggcac gagcgcttgc ttgcaggagc tgcgtctgca gtagcctggc cgctgacgct    240
gcgtgccggc tggcagggca gcctgcgacc tcgctggccc cgcgcccgct gctagccgcc    300
ggctccccac ctggttcgca cctagtccca gcccgggtcg cctgccgagt gcgcgcc atg   360
                                                                Met
                                                                  1 ggg ccg ccg ccc ggg atc ggg gtc tac tgc cgc ggc ggc tgc gga gct       408
Gly Pro Pro Pro Gly Ile Gly Val Tyr Cys Arg Gly Gly Cys Gly Ala
          5                  10                  15
```

```
gcc cgg cta ctg gct tgg tgc ttc ctt ctg gct ctg agt ccg cac gcg      456
Ala Arg Leu Leu Ala Trp Cys Phe Leu Leu Ala Leu Ser Pro His Ala
         20                  25                  30 ccc ggt tcc cgg gga gcc gaa gcc gtg tgg act gcg tac ctc aac gtg      504
Pro Gly Ser Arg Gly Ala Glu Ala Val Trp Thr Ala Tyr Leu Asn Val
 35                  40                  45 tcc tgg cgg gtt ccg cac acc gga gtg acc gca cgg tgt gga gct gag      552
Ser Trp Arg Val Pro His Thr Gly Val Thr Ala Arg Cys Gly Ala Glu
 50                  55                  60                  65 cga gag ggc gtg tac ggc cag gac tcg ccg ctg aag ccc gtc tcc ggg      600
Arg Glu Gly Val Tyr Gly Gln Asp Ser Pro Leu Lys Pro Val Ser Gly
                 70                  75                  80 gtc ctg gta ccg ccc gac ggg ccc ggg gcg ctc aac gcc tgt aac ccg      648
Val Leu Val Pro Pro Asp Gly Pro Gly Ala Leu Asn Ala Cys Asn Pro
             85                  90                  95 cac acc aat ttc acg gtg ccc acg gtt tgg ggg agc acg gtg caa gta      696
His Thr Asn Phe Thr Val Pro Thr Val Trp Gly Ser Thr Val Gln Val
            100                 105                 110 tct tgg ttg gcc ctc atc caa cgc ggt gga ggc tgc acc ttc gcg gac      744
Ser Trp Leu Ala Leu Ile Gln Arg Gly Gly Gly Cys Thr Phe Ala Asp
        115                 120                 125 aag atc cat ctg gct tca gag aga ggg gct tct gga gcg gtc atc ttt      792
Lys Ile His Leu Ala Ser Glu Arg Gly Ala Ser Gly Ala Val Ile Phe
130                 135                 140                 145 aac ttc cct ggg acc cgc aat gag gtc atc ccc atg tct cac ccg ggt      840
Asn Phe Pro Gly Thr Arg Asn Glu Val Ile Pro Met Ser His Pro Gly
                150                 155                 160 gct ggg gac att gtt gca atc atg att ggc aat ctg aaa gga aca aaa      888
Ala Gly Asp Ile Val Ala Ile Met Ile Gly Asn Leu Lys Gly Thr Lys
            165                 170                 175 att ctg cag tct att caa aga ggc atc caa gtc aca atg gtc atc gaa      936
Ile Leu Gln Ser Ile Gln Arg Gly Ile Gln Val Thr Met Val Ile Glu
        180                 185                 190 gta ggg aaa aaa cat ggc cct tgg gtg aat cat tat tca att ttc ttc      984
Val Gly Lys Lys His Gly Pro Trp Val Asn His Tyr Ser Ile Phe Phe
    195                 200                 205 gtt tct gtg tcc ttt ttc ata att acg gca gca acc gtg ggc tat ttc     1032
Val Ser Val Ser Phe Phe Ile Ile Thr Ala Ala Thr Val Gly Tyr Phe
210                 215                 220                 225 atc ttt tat tct gct cga aga tta cga aat gca aga gct caa agc agg     1080
Ile Phe Tyr Ser Ala Arg Arg Leu Arg Asn Ala Arg Ala Gln Ser Arg
                230                 235                 240 aag cag agg cag tta aag gca gat gct aaa aaa gct att gga aag ctt     1128
Lys Gln Arg Gln Leu Lys Ala Asp Ala Lys Lys Ala Ile Gly Lys Leu
            245                 250                 255 cag ctg cgc acc ttg aaa caa gga gac aag gaa att ggc cct gat gga     1176
Gln Leu Arg Thr Leu Lys Gln Gly Asp Lys Glu Ile Gly Pro Asp Gly
        260                 265                 270 gat agc tgt gct gtg tgc att gag ctc tat aag cca aat gat ttg gtg     1224
Asp Ser Cys Ala Val Cys Ile Glu Leu Tyr Lys Pro Asn Asp Leu Val
    275                 280                 285 cgc atc cta acc tgc aat cat att ttc cat aag aca tgt gtg gac ccg     1272
Arg Ile Leu Thr Cys Asn His Ile Phe His Lys Thr Cys Val Asp Pro
290                 295                 300                 305 tgg ctt tta gaa cac agg act tgc ccc atg tgc aag tgt gac att ctc     1320
Trp Leu Leu Glu His Arg Thr Cys Pro Met Cys Lys Cys Asp Ile Leu
                310                 315                 320 aaa gct ctg gga att gag gtg gat gtt gaa gat gga tca gtg tct tta     1368
Lys Ala Leu Gly Ile Glu Val Asp Val Glu Asp Gly Ser Val Ser Leu
```

-continued

```
           325                    330                    335
caa gtt cct gtt tct aat gaa gca tct aat act gcc tct ccc cat gaa    1416
Gln Val Pro Val Ser Asn Glu Ala Ser Asn Thr Ala Ser Pro His Glu
            340                    345                    350 gag gac agt cgc agt gag act gca tca tct gga tat gct tca gta caa    1464
Glu Asp Ser Arg Ser Glu Thr Ala Ser Ser Gly Tyr Ala Ser Val Gln
        355                    360                    365 gga gca gat gag cca cct ctg gag gaa cat gcg cag tca gca aat gaa    1512
Gly Ala Asp Glu Pro Pro Leu Glu Glu His Ala Gln Ser Ala Asn Glu
370                    375                    380                    385 aat cta cag ctg gta aac cat gaa gca aat tct gtg gcc gtg gat gtt    1560
Asn Leu Gln Leu Val Asn His Glu Ala Asn Ser Val Ala Val Asp Val
                390                    395                    400 gtt ccc cat gtt gac aac cca acc ttt gaa gaa gat gaa act cct gat    1608
Val Pro His Val Asp Asn Pro Thr Phe Glu Glu Asp Glu Thr Pro Asp
            405                    410                    415 caa gag gca gct gtt cgg gag att aaa tct taa aaatctgtgt caatagaaaa  1661
Gln Glu Ala Ala Val Arg Glu Ile Lys Ser *
        420                    425 cttgaaccgt tagttaacaa caggactgcc aatcagggcc tagtttacta tgaatgaact  1721
gggtaaacgt aaaacaagaa tgatactgaa agtgctgagg taacttatat tatactatag  1781
ttaaatggct taacatattt accccagtac cgttttccac aaactcacca taacgttttt  1841
cataggcaag tttcctcttg gtgatagtga tagcaacatt tttaacattc agaaccgtct  1901
atgagtagtc aggtttttca tttacaacaa ctttgttata aaaaaatatg ttgctttaaa  1961
agtgtggagt agctgtaatc actttgtttt atgatagtat cataattaaa caatactact  2021
actttagctt gggctctgtg tgtcggggtt tgtctccagg tgcttatatt gatctggaat  2081
ttgtttaaaa aaactcgtgc cgaattcttt ggatccacta gtgtcgacct gcaggcgcgc  2141
gagc                                                               2145

<210> SEQ ID NO 6
<211> LENGTH: 427
<212> TYPE: PRT
<213> ORGANISM: Mus musculus

<400> SEQUENCE: 6

Met Gly Pro Pro Gly Ile Gly Val Tyr Cys Arg Gly Cys Gly
1               5                   10                  15

Ala Ala Arg Leu Leu Ala Trp Cys Phe Leu Leu Ala Leu Ser Pro His
            20                  25                  30

Ala Pro Gly Ser Arg Gly Ala Glu Ala Val Trp Thr Ala Tyr Leu Asn
        35                  40                  45

Val Ser Trp Arg Val Pro His Thr Gly Val Thr Ala Arg Cys Gly Ala
    50                  55                  60

Glu Arg Glu Gly Val Tyr Gly Gln Asp Ser Pro Leu Lys Pro Val Ser
65                  70                  75                  80

Gly Val Leu Val Pro Pro Asp Gly Pro Gly Ala Leu Asn Ala Cys Asn
                85                  90                  95

Pro His Thr Asn Phe Thr Val Pro Thr Val Trp Gly Ser Thr Val Gln
            100                 105                 110

Val Ser Trp Leu Ala Leu Ile Gln Arg Gly Gly Gly Cys Thr Phe Ala
        115                 120                 125

Asp Lys Ile His Leu Ala Ser Glu Arg Gly Ala Ser Gly Ala Val Ile
    130                 135                 140
```

-continued

```
Phe Asn Phe Pro Gly Thr Arg Asn Glu Val Ile Pro Met Ser His Pro
145                 150                 155                 160

Gly Ala Gly Asp Ile Val Ala Ile Met Ile Gly Asn Leu Lys Gly Thr
            165                 170                 175

Lys Ile Leu Gln Ser Ile Gln Arg Gly Ile Gln Val Thr Met Val Ile
        180                 185                 190

Glu Val Gly Lys Lys His Gly Pro Trp Val Asn His Tyr Ser Ile Phe
    195                 200                 205

Phe Val Ser Val Ser Phe Phe Ile Ile Thr Ala Ala Thr Val Gly Tyr
210                 215                 220

Phe Ile Phe Tyr Ser Ala Arg Arg Leu Arg Asn Ala Arg Ala Gln Ser
225                 230                 235                 240

Arg Lys Gln Arg Gln Leu Lys Ala Asp Ala Lys Lys Ala Ile Gly Lys
            245                 250                 255

Leu Gln Leu Arg Thr Leu Lys Gln Gly Asp Lys Glu Ile Gly Pro Asp
        260                 265                 270

Gly Asp Ser Cys Ala Val Cys Ile Glu Leu Tyr Lys Pro Asn Asp Leu
    275                 280                 285

Val Arg Ile Leu Thr Cys Asn His Ile Phe His Lys Thr Cys Val Asp
290                 295                 300

Pro Trp Leu Leu Glu His Arg Thr Cys Pro Met Cys Lys Cys Asp Ile
305                 310                 315                 320

Leu Lys Ala Leu Gly Ile Glu Val Asp Val Glu Asp Gly Ser Val Ser
            325                 330                 335

Leu Gln Val Pro Val Ser Asn Glu Ala Ser Asn Thr Ala Ser Pro His
        340                 345                 350

Glu Glu Asp Ser Arg Ser Glu Thr Ala Ser Ser Gly Tyr Ala Ser Val
    355                 360                 365

Gln Gly Ala Asp Glu Pro Pro Leu Glu Glu His Ala Gln Ser Ala Asn
370                 375                 380

Glu Asn Leu Gln Leu Val Asn His Glu Ala Asn Ser Val Ala Val Asp
385                 390                 395                 400

Val Val Pro His Val Asp Asn Pro Thr Phe Glu Glu Asp Glu Thr Pro
            405                 410                 415

Asp Gln Glu Ala Ala Val Arg Glu Ile Lys Ser
        420                 425
```

<210> SEQ ID NO 7
<211> LENGTH: 1774
<212> TYPE: DNA
<213> ORGANISM: Homo sapiens
<220> FEATURE:
<221> NAME/KEY: CDS
<222> LOCATION: (263)...(1547)
<221> NAME/KEY: misc_feature
<222> LOCATION: (1)...(1774)
<223> OTHER INFORMATION: n = A,T,C or G

<400> SEQUENCE: 7

```
agctggagct ccaccgcggt ggcggccgct ctagaactag tggatccccc gggctgcagg      60
aattcggcac gagccgagga gctgcatctg cggcaacctg tgtgctgacg ctacgtgcct     120
cctggctccg acgtagctcg cagctcccca gtctcactcc attccttccc cacctggcgc     180
gcacctgctc aagaccaggg tcctgccaag cgctaggagg cgcgcgtgcca ggggcgctag    240 ggaactgcgg agcgcgcgcg cc atg ggg ccg ccg cct ggg gcc ggg gtc tcc      292
                           Met Gly Pro Pro Pro Gly Ala Gly Val Ser
                             1               5                  10
```

| | |
|---|---|
| tgc cgc ggt ggc tgc ggc ttt tcc aga ttg ctg gca tgg tgc ttc ctg<br>Cys Arg Gly Gly Cys Gly Phe Ser Arg Leu Leu Ala Trp Cys Phe Leu<br>                              15                      20                    25 | 340 |
| ctg gcc ctg agt ccg cag gca ccc ggt tcc cgg ggg gct gaa gca gtg<br>Leu Ala Leu Ser Pro Gln Ala Pro Gly Ser Arg Gly Ala Glu Ala Val<br>                   30                      35                          40 | 388 |
| tgg acc gcg tac ctc aac gtg tcc tgg cgg gtt ccg cac acg gga gtg<br>Trp Thr Ala Tyr Leu Asn Val Ser Trp Arg Val Pro His Thr Gly Val<br>        45                      50                          55 | 436 |
| aac cgt acg gtg tgg gag ctg agc gag gag ggc gtg tac ggc cag gac<br>Asn Arg Thr Val Trp Glu Leu Ser Glu Glu Gly Val Tyr Gly Gln Asp<br>            60                      65                          70 | 484 |
| tcg ccg ctg gag cct gtg gct ggg gtc ctg gta ccg ccc gac ggg ccc<br>Ser Pro Leu Glu Pro Val Ala Gly Val Leu Val Pro Pro Asp Gly Pro<br>75                      80                      85                          90 | 532 |
| ggg gcg ctt aac gcc tgt aac ccg cac acg aat ttc acg gtg ccc acg<br>Gly Ala Leu Asn Ala Cys Asn Pro His Thr Asn Phe Thr Val Pro Thr<br>                              95                     100                   105 | 580 |
| gtt tgg gga agc acc gtg caa gtc tct tgg ttg gcc ctc atc caa cgc<br>Val Trp Gly Ser Thr Val Gln Val Ser Trp Leu Ala Leu Ile Gln Arg<br>                110                      115                     120 | 628 |
| ggc ggg ggc tgc acc ttc gca gac aag atc cat ctg gct tat gag aga<br>Gly Gly Gly Cys Thr Phe Ala Asp Lys Ile His Leu Ala Tyr Glu Arg<br>                125                     130                    135 | 676 |
| tgg gcg tct gga gcc gtc atc ttt aac ttc ccc ggg acc cgc aat gag<br>Trp Ala Ser Gly Ala Val Ile Phe Asn Phe Pro Gly Thr Arg Asn Glu<br>          140                     145                     150 | 724 |
| gtc atc ccc atg tct cac ccg ggt gca gta gac att gtt gca atc atg<br>Val Ile Pro Met Ser His Pro Gly Ala Val Asp Ile Val Ala Ile Met<br>155                      160                     165                     170 | 772 |
| atc ggc aat ctg aaa ggc aca aaa att ctg caa tct att caa aga ggc<br>Ile Gly Asn Leu Lys Gly Thr Lys Ile Leu Gln Ser Ile Gln Arg Gly<br>                175                     180                    185 | 820 |
| ata caa gtg aca atg gtc ata gaa gta ggg aaa aaa cat ggc cct tgg<br>Ile Gln Val Thr Met Val Ile Glu Val Gly Lys Lys His Gly Pro Trp<br>                   190                     195                    200 | 868 |
| gtg aat cac tat tca att ttt ttc gtt tct gtg tcc ttt ttt att att<br>Val Asn His Tyr Ser Ile Phe Phe Val Ser Val Ser Phe Phe Ile Ile<br>          205                     210                     215 | 916 |
| acg gcg gca act gtg ggc tat ttt atc ttt tat tct gct cga agg cta<br>Thr Ala Ala Thr Val Gly Tyr Phe Ile Phe Tyr Ser Ala Arg Arg Leu<br>220                      225                     230 | 964 |
| cgg aat gca aga gct caa agc agg aag cag agg caa tta aag gca gat<br>Arg Asn Ala Arg Ala Gln Ser Arg Lys Gln Arg Gln Leu Lys Ala Asp<br>235                      240                     245                    250 | 1012 |
| gct aaa aaa gct att gga agg ctt caa cta cgc aca ctg aaa caa gga<br>Ala Lys Lys Ala Ile Gly Arg Leu Gln Leu Arg Thr Leu Lys Gln Gly<br>                   255                     260                    265 | 1060 |
| gac aag gaa att ggc cct gat gga gat agt tgt gct gtg tgc att gaa<br>Asp Lys Glu Ile Gly Pro Asp Gly Asp Ser Cys Ala Val Cys Ile Glu<br>                   270                     275                    280 | 1108 |
| ttg tat aaa cca aat gat ttg gta cgc atc tta acg tgc aac cat att<br>Leu Tyr Lys Pro Asn Asp Leu Val Arg Ile Leu Thr Cys Asn His Ile<br>          285                     290                     295 | 1156 |
| ttc cat aag aca tgt gtt gac cca tgg ctg tta aaa cac aag act tgc<br>Phe His Lys Thr Cys Val Asp Pro Trp Leu Leu Lys His Lys Thr Cys<br>300                      305                     310 | 1204 |
| ccc atg tgc aaa tgt gac ata ctc aaa gct ttg gga att gag gtg gat<br>Pro Met Cys Lys Cys Asp Ile Leu Lys Ala Leu Gly Ile Glu Val Asp | 1252 |

-continued

```
              315                 320                 325                 330
gtt gaa gat gga tca gtg tct tta caa gtc cct gta tcc aat gaa ata           1300
Val Glu Asp Gly Ser Val Ser Leu Gln Val Pro Val Ser Asn Glu Ile
                    335                 340                 345 tct aat agt gcc tcc tcc cat gaa gag gat aat cgc agc gag acc gca           1348
Ser Asn Ser Ala Ser Ser His Glu Glu Asp Asn Arg Ser Glu Thr Ala
            350                 355                 360 tca tct gga tat gct tca gta cag gga aca gat gaa ccg cct ctg gag           1396
Ser Ser Gly Tyr Ala Ser Val Gln Gly Thr Asp Glu Pro Pro Leu Glu
        365                 370                 375 gaa cac gtg cag tca aca aat gaa agt cta cag ctg gta aac cat gaa           1444
Glu His Val Gln Ser Thr Asn Glu Ser Leu Gln Leu Val Asn His Glu
    380                 385                 390 gca aat tct gtg gca gtg gat gtt att cct cat gtn gac aac cca acc           1492
Ala Asn Ser Val Ala Val Asp Val Ile Pro His Val Asp Asn Pro Thr
395                 400                 405                 410 ttt gaa gaa gac gaa act cct aat caa gag act gct gtt cga gaa att           1540
Phe Glu Glu Asp Glu Thr Pro Asn Gln Glu Thr Ala Val Arg Glu Ile
                415                 420                 425 aaa tct t aaaatctgtg taaatagaaa acttgaacca ttagtaataa cagaactgcc          1597
Lys Ser aatcagggcc tagtttctat taataaattg gataaattta ataaaataag agtgatactg         1657
aaagtgctca gatgactaat attatgctat agttaaaatg gcttaaaaat atttaacctg         1717 ttaactttt tccaccaaac tcattataat attttttcata ggcaagtttc ctctcag            1774
```

<210> SEQ ID NO 8
<211> LENGTH: 428
<212> TYPE: PRT
<213> ORGANISM: Homo sapiens

<400> SEQUENCE: 8

```
Met Gly Pro Pro Pro Gly Ala Gly Val Ser Cys Arg Gly Gly Cys Gly
  1               5                  10                  15

Phe Ser Arg Leu Leu Ala Trp Cys Phe Leu Leu Ala Leu Ser Pro Gln
             20                  25                  30

Ala Pro Gly Ser Arg Gly Ala Glu Ala Val Trp Thr Ala Tyr Leu Asn
         35                  40                  45

Val Ser Trp Arg Val Pro His Thr Gly Val Asn Arg Thr Val Trp Glu
     50                  55                  60

Leu Ser Glu Glu Gly Val Tyr Gly Gln Asp Ser Pro Leu Glu Pro Val
 65                  70                  75                  80

Ala Gly Val Leu Val Pro Pro Asp Gly Pro Gly Ala Leu Asn Ala Cys
                 85                  90                  95

Asn Pro His Thr Asn Phe Thr Val Pro Thr Val Trp Gly Ser Thr Val
            100                 105                 110

Gln Val Ser Trp Leu Ala Leu Ile Gln Arg Gly Gly Gly Cys Thr Phe
        115                 120                 125

Ala Asp Lys Ile His Leu Ala Tyr Glu Arg Trp Ala Ser Gly Ala Val
    130                 135                 140

Ile Phe Asn Phe Pro Gly Thr Arg Asn Glu Val Ile Pro Met Ser His
145                 150                 155                 160

Pro Gly Ala Val Asp Ile Val Ala Ile Met Ile Gly Asn Leu Lys Gly
                165                 170                 175

Thr Lys Ile Leu Gln Ser Ile Gln Arg Gly Ile Gln Val Thr Met Val
            180                 185                 190
```

-continued

```
Ile Glu Val Gly Lys Lys His Gly Pro Trp Val Asn His Tyr Ser Ile
    195             200             205

Phe Phe Val Ser Val Ser Phe Phe Ile Ile Thr Ala Ala Thr Val Gly
    210             215             220

Tyr Phe Ile Phe Tyr Ser Ala Arg Arg Leu Arg Asn Ala Arg Ala Gln
225             230             235             240

Ser Arg Lys Gln Arg Gln Leu Lys Ala Asp Ala Lys Lys Ala Ile Gly
            245             250             255

Arg Leu Gln Leu Arg Thr Leu Lys Gln Gly Asp Lys Glu Ile Gly Pro
            260             265             270

Asp Gly Asp Ser Cys Ala Val Cys Ile Glu Leu Tyr Lys Pro Asn Asp
            275             280             285

Leu Val Arg Ile Leu Thr Cys Asn His Ile Phe His Lys Thr Cys Val
    290             295             300

Asp Pro Trp Leu Leu Lys His Lys Thr Cys Pro Met Cys Lys Cys Asp
305             310             315             320

Ile Leu Lys Ala Leu Gly Ile Glu Val Asp Val Glu Asp Gly Ser Val
            325             330             335

Ser Leu Gln Val Pro Val Ser Asn Glu Ile Ser Asn Ser Ala Ser Ser
            340             345             350

His Glu Glu Asp Asn Arg Ser Glu Thr Ala Ser Ser Gly Tyr Ala Ser
            355             360             365

Val Gln Gly Thr Asp Glu Pro Pro Leu Glu Glu His Val Gln Ser Thr
    370             375             380

Asn Glu Ser Leu Gln Leu Val Asn His Glu Ala Asn Ser Val Ala Val
385             390             395             400

Asp Val Ile Pro His Val Asp Asn Pro Thr Phe Glu Glu Asp Glu Thr
            405             410             415

Pro Asn Gln Glu Thr Ala Val Arg Glu Ile Lys Ser
            420             425
```